(12) United States Patent
Balko et al.

(10) Patent No.: US 7,498,468 B2
(45) Date of Patent: Mar. 3, 2009

(54) 6-(POLY-SUBSTITUTED ARYL)-4-AMINOPICOLINATES AND THEIR USE AS HERBICIDES

(75) Inventors: Terry W. Balko, Greenfield, IN (US); John F. Daeuble, Carmel, IN (US); Thomas L. Siddall, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 11/906,972

(22) Filed: Oct. 4, 2007

(65) Prior Publication Data

US 2008/0045734 A1 Feb. 21, 2008

Related U.S. Application Data

(62) Division of application No. 11/653,042, filed on Jan. 12, 2007, now Pat. No. 7,314,849.

(60) Provisional application No. 60/758,701, filed on Jan. 13, 2006, provisional application No. 60/850,145, filed on Oct. 6, 2006.

(51) Int. Cl.
*C07F 5/02* (2006.01)
*C07F 7/22* (2006.01)
*C07F 3/02* (2006.01)
*C07F 3/06* (2006.01)
*C07C 25/13* (2006.01)
*C07C 39/27* (2006.01)
*C07C 39/28* (2006.01)
*C07C 47/55* (2006.01)
*C07C 49/80* (2006.01)

(52) U.S. Cl. .......................... 568/1; 568/656; 568/775; 570/127; 570/162; 570/171

(58) Field of Classification Search ............... 568/1, 568/656, 775; 570/127, 162, 171
See application file for complete search history.

(56) References Cited

U.S. PATENT DOCUMENTS 6,784,137 B2 8/2004 Balko et al.
2007/0179059 A1 8/2007 Epp et al.

FOREIGN PATENT DOCUMENTS

WO WO-2005/063721 A1 * 7/2005

OTHER PUBLICATIONS

Search Report for PCT/US2007/000994 [filed Jan. 12, 2007] including non-US patent cited references, Sep. 6, 2007, Dow AgroSciences LLC [Terry W. Balko, et al.].

* cited by examiner

*Primary Examiner*—Venkataraman Balasubramanian
(74) *Attorney, Agent, or Firm*—Craig Mixan

(57) ABSTRACT

4-Aminopicolinic acids having tri- and tetra-substituted aryl substituents in the 6-position, and their amine and acid derivatives, are potent herbicides demonstrating a broad spectrum of weed control.

2 Claims, No Drawings

6-(POLY-SUBSTITUTED ARYL)-4-AMINOPICOLINATES AND THEIR USE AS HERBICIDES

This application is a divisional of U.S. application Ser. No. 11/653,042 filed Jan. 12, 2007, now U.S. Pat. No. 7,314,849, claiming the benefits of U.S. Provisional Application No. 60/758,701 filed Jan. 13, 2006 and U.S. Provisional Application No. 60/850,145 filed Oct. 6, 2006.

BACKGROUND OF THE INVENTION

This invention relates to certain novel 6-(poly-substituted aryl)-4-aminopicolinates and their derivatives and to the use of these compounds as herbicides.

A number of picolinic acids and their pesticidal properties have been described in the art. U.S. Pat. No. 6,784,137 B2 discloses a genus of 6-aryl-4-aminopicolinic acids and their derivatives and their use as herbicides. It has now been discovered that certain particular subclasses of the genus disclosed in '137 have greatly improved herbicidal activity and selectivity.

SUMMARY OF THE INVENTION

It has now been found that certain 6-(poly-substituted aryl)-4-aminopicolinic acids and their derivatives are superior herbicides with a broad spectrum of weed control against woody plants, grasses and sedges as well as broadleaves and with excellent crop selectivity. The compounds further possess excellent toxicological or environmental profiles.

The invention includes compounds of Formula I:

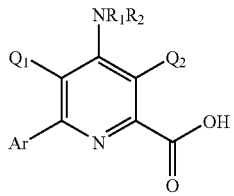

I wherein
$Q_1$ represents H or F;
$Q_2$ represents a halogen with the proviso that when $Q_1$ is H then $Q_2$ is Cl or Br;
$R_1$ and $R_2$ independently represent H, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl or $C_1$-$C_6$ dialkyl phosphonyl or $R_1$ and $R_2$ taken together with N represent a 5- or 6-membered saturated ring; and
Ar represents a polysubstituted aryl group selected from the group consisting of a)

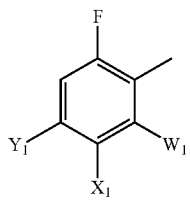

wherein
$W_1$ represents halogen;
$X_1$ represents F, Cl, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkyl, $C_1$-$C_4$ haloalkoxy, $C_1$-$C_4$ alkoxy-substituted $C_1$-$C_4$ alkyl, $C_1$-$C_4$ alkoxy-substituted $C_1$-$C_4$ alkoxy, —CN, —$NR_3R_4$ or fluorinated acetyl or propionyl;
$Y_1$ represents $C_1$-$C_4$ alkyl, $C_1$-$C_4$ haloalkyl, halogen or —CN, or, when $X_1$ and $Y_1$ are taken together, represents —$O(CH_2)_nO$— wherein n=1 or 2; and
$R_3$ and $R_4$ independently represent H or $C_1$-$C_4$ alkyl;

b)

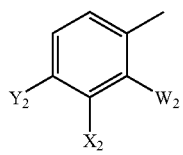

wherein
$W_2$ represents F or Cl;
$X_2$ represents F, Cl, —CN, —$NO_2$, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkyl, $C_1$-$C_4$ haloalkoxy, $C_1$-$C_4$ alkoxy-substituted $C_1$-$C_4$ alkyl, $C_1$-$C_4$ alkoxy-substituted $C_1$-$C_4$ alkoxy, —$NR_3R_4$ or fluorinated acetyl or propionyl;
$Y_2$ represents halogen, $C_1$-$C_4$ alkyl, $C_1$-$C_4$ haloalkyl or —CN, or, when $W_2$ represents F, $X_2$ and $Y_2$ taken together represent —$O(CH_2)_nO$— wherein n=1 or 2; and
$R_3$ and $R_4$ independently represent H or $C_1$-$C_6$ alkyl; and c)

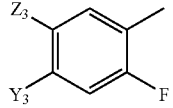

wherein
$Y_3$ represents halogen, —CN or —$CF_3$;
$Z_3$ represents F, Cl, —CN, —$NO_2$, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkyl, $C_1$-$C_4$ haloalkoxy, $C_1$-$C_4$ alkoxy-substituted $C_1$-$C_4$ alkyl, $C_1$-$C_4$ alkoxy-substituted $C_1$-$C_4$ alkoxy, —$NR_3R_4$ or fluorinated acetyl or propionyl; and
$R_3$ and $R_4$ independently represent H, or $C_1$-$C_6$ alkyl;

and agriculturally acceptable derivatives of the carboxylic acid group.

Compounds of Formula I wherein $Y_1$, $Y_2$ or $Y_3$ represents Cl, Br or $CF_3$, wherein $W_1$ or $W_2$ represents Cl or F, wherein $X_1$ or $X_2$ represents $C_1$-$C_4$ alkoxy, $C_1$-$C_4$ thioalkoxy, $C_1$-$C_4$ haloalkyl or $NR_3R_4$, and wherein Z represents $C_1$-$C_4$ alkoxy, $C_1$-$C_4$ thioalkoxy, $C_1$-$C_4$ haloalkyl or $NR_3R_4$ are independently preferred.

The invention includes herbicidal compositions comprising a herbicidally effective amount of a compound of Formula I and agriculturally acceptable derivatives of the carboxylic acid group in admixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil prior to emergence of the vegetation. The invention further includes intermediates for the preparation of the compounds.

DETAILED DESCRIPTION OF THE INVENTION

The herbicidal compounds of the present invention are derivatives of 4-aminopicolinic acids of Formula II:

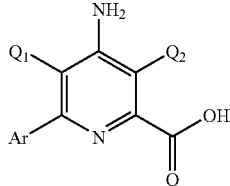

wherein
$Q_1$ represents H or F;
$Q_2$ represents a halogen with the proviso that when $Q_1$ is H then $Q_2$ is Cl or Br; and
Ar represents a polysubstituted aryl group selected from the group consisting of a)

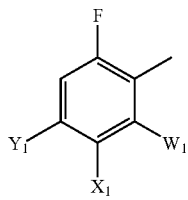

wherein
$W_1$ represents halogen;
$X_1$ represents F, Cl, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkyl, $C_1$-$C_4$ haloalkoxy, $C_1$-$C_4$ alkoxy-substituted $C_1$-$C_4$ alkyl, $C_1$-$C_4$ alkoxy-substituted $C_1$-$C_4$ alkoxy, —CN, fluorinated acetyl or propionyl, or —NR$_3$R$_4$;
$Y^1$ represents $C_1$-$C_4$ alkyl, $C_1$-$C_4$ haloalkyl, halogen or —CN or, when $X_1$ and $Y_1$ are taken together, represents —O(CH$_2$)$_n$O— wherein n=1 or 2; and
$R_3$ and $R_4$ independently represent H, or $C_1$-$C_4$ alkyl;

b)

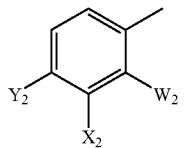

wherein
$W_2$ represents F or Cl;
$X_2$ represents, F, Cl, —CN, —NO$_2$, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkyl, $C_1$-$C_4$ haloalkoxy, $C_1$-$C_4$ alkoxy-substituted $C_1$-$C_4$ alkyl, $C_1$-$C_4$ alkoxy-substituted $C_1$-$C_4$ alkoxy, fluorinated acetyl or propionyl, or —NR$_3$R$_4$;

$Y_2$ represents halogen, $C_1$-$C_4$ alkyl, $C_1$-$C_4$ haloalkyl or —CN, or, when $W_2$ represents F, $X_2$ and $Y_2$ taken together represent —O(CH$_2$)$_n$O— wherein n=1 or 2; and
$R_3$ and $R_4$ independently represent H, or $C_1$-$C_6$ alkyl; and c)

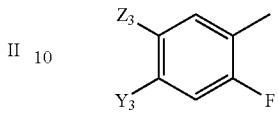

wherein
$Y_3$ represents halogen, —CN or —CF$_3$;
$Z_3$ represents F, Cl, —CN, —NO$_2$, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkyl, $C_1$-$C_4$ haloalkoxy, $C_1$-$C_4$ alkoxy-substituted $C_1$-$C_4$ alkyl, $C_1$-$C_4$ alkoxy-substituted $C_1$-$C_4$ alkoxy fluorinated acetyl or propionyl, or —NR$_3$R$_4$; and
$R_3$ and $R_4$ independently represent H, or $C_1$-$C_6$ alkyl.

These compounds are characterized by possessing a Cl or F in the 3-position, H or F in the 5-position and a tri- or tetra-substituted aryl group in the 6-position of the pyridine ring. Compounds in which Cl is in the 3-position and H is in the 5-position are generally preferred. Preferred substituted aryl groups include 2,3,4-trisubstituted, 2-fluoro-4,5-trisubstituted and 2-fluoro-4,5,6-tetrasubstituted phenyl groups. Particularly preferred substituted aryl groups include those wherein $Y_1$, $Y_2$ or $Y_3$ represents Cl, Br or CF$_3$, wherein $W_1$ or $W_2$ represents Cl or F, wherein $X_1$ or $X_2$ represents $C_1$-$C_4$ alkoxy, $C_1$-$C_4$ thioalkoxy, $C_1$-$C_4$ haloalkyl or NR$_3$R$_4$, and wherein Z represents $C_1$-$C_4$ alkoxy, $C_1$-$C_4$ thioalkoxy, $C_1$-$C_4$ haloalkyl or NR$_3$R$_4$.

The amino group at the 4-position of the pyridine ring can be unsubstituted or substituted with one or more $C_1$-$C_6$ alkyl, $C_3$-$C_6$ alkenyl, $C_3$-$C_6$ alkynyl, hydroxy, $C_1$-$C_6$ alkoxy or amino substituents. The amino group can be further derivatized as an amide, a carbamate, a urea, a sulfonamide, a silylamine or a phosphoramidate. Such derivatives are capable of breaking down into the amine. An unsubstituted amino group is preferred.

The carboxylic acids of Formula I are believed to be the compounds that actually kill or control undesirable vegetation and are typically preferred. Analogs of these compounds in which the acid group of the picolinic acid is derivatized to form a related substituent that can be transformed within plants or the environment to a acid group possess essentially the same herbicidal effect and are within the scope of the invention. Therefore, an "agriculturally acceptable derivative", when used to describe the carboxylic acid functionality at the 2-position, is defined as any salt, ester, acylhydrazide, imidate, thioimidate, amidine, amide, orthoester, acylcyanide, acyl halide, thioester, thionoester, dithiolester, nitrile or any other acid derivative well known in the art which (a) does not substantially affect the herbicidal activity of the active ingredient, i.e., the 6-aryl-4-aminopicolinic acid, and (b) is or can be hydrolyzed, oxidized or metabolized in plants or soil to the picolinic acid of Formula I that, depending upon the pH, is in the dissociated or the undissociated form. The preferred agriculturally acceptable derivatives of the carboxylic acid are agriculturally acceptable salts, esters and amides. Likewise, an "agriculturally acceptable derivative", when used to describe the amine functionality at the 4-position, is defined as any salt, silylamine, phosphorylamine, phosphinimine, phosphoramidate, sulfonamide, sulfilimine, sulfoximine, aminal, hemiaminal, amide, thioamide, carbamate, thiocarbamate, amidine, urea, imine, nitro, nitroso, azide, or any other nitrogen containing derivative well known in the art which (a) does not substantially affect the herbicidal activity of the active ingredient, i.e., the 6-aryl-4-aminopicolinic acid, and (b) is or can be hydrolyzed in plants or soil to a free amine of Formula II. N-Oxides, which are also capable of breaking into the parent picoline of Formula II, are also covered by the scope of this invention.

Suitable salts include those derived from alkali or alkaline earth metals and those derived from ammonia and amines. Preferred cations include sodium, potassium, magnesium, and aminium cations of the formula:

$R_5R_6R_7NH^+$ wherein $R_5$, $R_6$, and $R_7$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R_5$, $R_6$, and $R_7$ are sterically compatible. Additionally, any two of $R_5$, $R_6$, and $R_7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of Formula I because they are water-soluble and lend themselves to the preparation of desirable aqueous based herbicidal compositions.

Suitable esters include those derived from $C_1$-$C_{12}$ alkyl, $C_3$-$C_{12}$ alkenyl or $C_3$-$C_{12}$ alkynyl alcohols, such as methanol, iso-propanol, butanol, 2-ethylhexanol, butoxyethanol, methoxypropanol, allyl alcohol, propargyl alcohol or cyclohexanol. Esters can be prepared by coupling of the picolinic acid with the alcohol using any number of suitable activating agents such as those used for peptide couplings such as dicyclohexylcarbodiimide (DCC) or carbonyl diimidazole (CDI), by reacting the corresponding acid chloride of a picolinic acid of Formula I with an appropriate alcohol or by reacting the corresponding picolinic acid of Formula I with an appropriate alcohol in the presence of an acid catalyst. Suitable amides include those derived from ammonia or from $C_1$-$C_{12}$ alkyl, $C_3$-$C_{12}$ alkenyl or $C_3$-$C_{12}$ alkynyl mono- or di-substituted amines, such as but not limited to dimethylamine, diethanolamine, 2-methylthiopropylamine, bisallylamine, 2-butoxyethylamine, cyclododecylamine, benzylamine or cyclic or aromatic amines with or without additional heteroatoms such as but not limited to aziridine, azetidine, pyrrolidine, pyrrole, imidazole, tetrazole or morpholine. Amides can be prepared by reacting the corresponding picolinic acid chloride, mixed anhydride, or carboxylic ester of Formula I with ammonia or an appropriate amine.

The terms "alkyl", "alkenyl" and "alkynyl", as well as derivative terms such as "alkoxy", "acyl", "alkylthio" and "alkylsulfonyl", as used herein, include within their scope straight chain, branched chain and cyclic moieties. The terms "alkenyl" and "alkynyl" are intended to include one or more unsaturated bonds.

The term "aryl", as well as derivative terms such as "aryloxy", refers to a phenyl.

Unless specifically limited otherwise, the term "halogen" including derivative terms such as "halo" refers to fluorine, chlorine, bromine, and iodine. The terms "haloalkyl" and "haloalkoxy" refer to alkyl and alkoxy groups substituted with from 1 to the maximum possible number of halogen atoms.

The compounds of Formula I can be made using well-known chemical procedures. The required starting materials are commercially available or readily synthesized utilizing standard procedures.

The 6-substituted arylpicolines of Formula I can be prepared from a number of ways, which are well known in the art, e.g., by reaction of an appropriately substituted pyridine with a facile leaving group in the 6-position (III) with an organometallic compound of the type (IV) in an inert solvent in the presence of a transition metal catalyst.

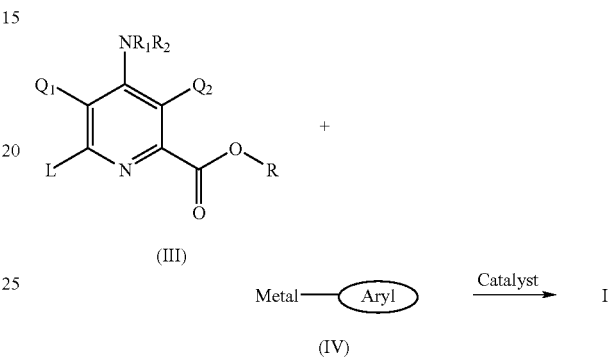

In this case "L" can be chlorine, bromine, iodo or trifluoromethanesulfonate, "Metal" can be Mg-halide, Zn-halide, tri-($C_1$-$C_4$ alkyl)tin, lithium, copper, or $B(OR_8)(OR_9)$, where $R_8$ and $R_9$ are, independent of one another, hydrogen, $C_1$-$C_4$ alkyl, or when taken together form an ethylene or propylene group, and "Catalyst" is a transition metal catalyst, in particular a palladium catalyst such as palladium diacetate, bis(triphenylphosphine)palladium(II)dichloride, or a nickel catalyst such as nickel(II)acetylacetonate, bis(triphenylphosphine)nickel(II)chloride.

Alternatively, compounds of Formula I can be prepared by reaction of an appropriately substituted 6-metal substituted pyridine (V) with an aryl compound of the type (VI) in an inert solvent in the presence of a transition metal catalyst.

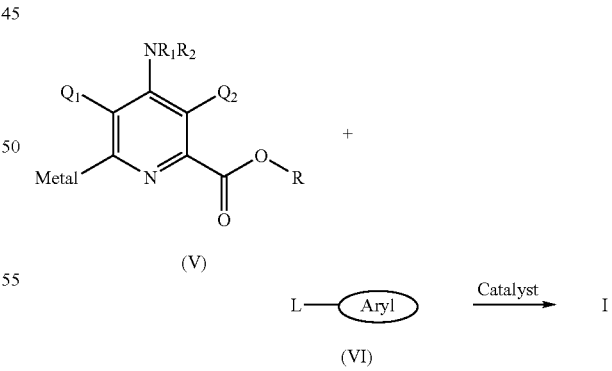

In this case "L" can be chlorine, bromine, iodo or trifluoromethanesulfonate and "Metal" can be Mg-halide, Zn-halide, tri-($C_1$-$C_4$ alkyl)tin, lithium, copper, or $B(OR_8)(OR_9)$, where $R_8$ and $R_9$ are independent of one another, hydrogen, $C_1$-$C_4$ alkyl, or when taken together form an ethylene or propylene group, and "Catalyst" can be a transition metal catalyst, in particular a palladium catalyst such as palladium diacetate, bis(triphenylphosphine)palladium(II)dichloride, or a nickel catalyst such as nickel(II)acetylacetonate, bis(triphenylphosphine)nickel(II)chloride.

Reactions with boronic acids or esters are well known as exemplified by the following references:
(1) W. J. Thompson and J. Gaudino, J. Org. Chem., 49, 5223 (1984);
(2) S. Gronowitz and K. Lawitz, Chem. Scr., 24, 5 (1984);
(3) S. Gronowitz et al., Chem. Scr., 26, 305 (1986);
(4) J. Stavenuiter et al., Heterocycles, 26, 2711 (1987);
(5) V. Snieckus et al., Tetrahedron Letters, 28, 5093 (1987);
(6) V. Snieckus et al., Tetrahedron Letters, 29, 2135 (1988);
(7) M. B. Mitchell et al., Tetrahedron Letters, 32, 2273 (1991); Tetrahedron, 48, 8117 (1992);
(8) JP-A 93/301870.

Reactions with Grignard compounds (metal=Mg-Hal):
(9) L. N. Pridgen, J. Heterocyclic Chem., 12, 443 (1975);
(10) M. Kumada et al., Tetrahedron Letters, 21, 845 (1980);
(11) A. Minato et al., J. Chem. Soc. Chem. Commun., 5319 (1984).

Reaction with organozinc compounds (metal=Zn-Hal):
(12) A. S. Bell et al., Synthesis, 843 (1987);
(13) A. S. Bell et al., Tetrahedron Letters, 29, 5013 (1988);
(14) J. W. Tilley and S. Zawoiski, J. Org. Chem., 53, 386 (1988); see also ref. (9).

Reactions with organotin compounds (metal=Sn($C_1$-$C_4$ (alkyl)$_3$):
(15) T. R. Bailey et al., Tetrahedron Letters, 27, 4407 (1986);
(16) Y. Yamamoto et al., Synthesis, 564 (1986); see also ref. (6)

The coupling of III+IV, or V+VI may, where appropriate, be followed by reactions on either ring to obtain further derivatives of the compounds of Formula I.

Appropriately substituted pyridines of Formula III where L is chloro, bromo, iodo or trifluoromethanesulfonate can be easily obtain by well-known methods; see WO 0151468. For example, 6-bromo analogs can be prepared by the reduction of several key intermediates, e.g., the corresponding 6-bromo-4-azido, 6-bromo-4-nitro, and 6-bromo-4-nitro pyridine N-oxide analogs. These intermediates, in turn, can be prepared either by nucleophilic displacement of 6-bromo-4-halo analogs with $NaN_3$ or by electrophilic nitration of the corresponding 6-bromopyridine-N-oxides. Alternatively, such analogs can be prepared by direct amination of the corresponding 4,6-dibromo analogs.

4-N-Amide, carbamate, urea, sulfonamide, silylamine and phosphoramidate amino derivatives can be prepared by the reaction of the free amino compound with, for example, a suitable acid halide, chloroformate, carbamyl chloride, sulfonyl chloride, silyl chloride or chlorophosphate.

Substituted 4-amino analogs can be prepared by reacting the corresponding 4-halopyridine-2-carboxylate or any other displaceable 4-substituent with the substituted amine.

The compounds of Formula I, obtained by any of these processes, can be recovered by conventional means. Typically, the reaction mixture is acidified with an aqueous acid, such as hydrochloric acid, and extracted with an organic solvent, such as ethyl acetate or methylene chloride. The organic solvent and other volatiles can be removed by distillation or evaporation to obtain the desired compound of Formula I, which can be purified by standard procedures, such as by recrystallization or chromatography.

The compounds of Formula I have been found to be useful as pre-emergence and post-emergence herbicides. They can be employed at non-selective (higher) rates of application to control a broad spectrum of the vegetation in an area or at lower rates of application for the selective control of undesirable vegetation. Areas of application include pasture and rangelands, roadsides and rights of way, power lines and any industrial areas where control of undesirable vegetation is desirable. Another use is the control of unwanted vegetation in crops such as corn, rice and cereals. They can also be used to control undesirable vegetation in tree crops such as citrus, apple, rubber, oil palm, forestry and others. It is usually preferred to employ the compounds post-emergence. It is further usually preferred to use the compounds to control a wide spectrum of woody plants, broadleaf and grass weeds, and sedges. Use of the compounds to control undesirable vegetation in established crops is especially indicated. While each of the 6-aryl-4-aminopicolinate compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I postemergence to relatively immature undesirable vegetation to achieve the maximum control of weeds.

Application rates of about 0.1 to about 1,000 g/Ha are generally employed in postemergence operations; for preemergence applications, rates of about 1 to about 2,000 g/Ha are generally employed. The higher rates designated generally give non-selective control of a broad variety of undesirable vegetation. The lower rates typically give selective control and can be employed in the locus of crops.

The herbicidal compounds of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmediphamethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlomitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac. The herbicidal compounds of the present invention can, further, be used in conjunction with glyphosate, glufosinate or 2,4-D on glyphosate-tolerant, glufosinate-tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The compounds of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyrdiethyl, MG 191, MON 4660, naphthalic anhydride (NA), oxabetrinil, R29148 and N-phenylsulfonylbenzoic acid amides, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are acetolactate synthase inhibitors in sensitive plants can be treated. Many glyphosate and glufosinate tolerant crops can be treated as well, alone or in combination with these herbicides. Some crops (e.g. cotton) have been made tolerant to auxinic herbicides such as 2,4-dichlorophenoxyacetic acid. These herbicides may be used to treat such resistant crops or other auxin tolerant crops.

While it is possible to utilize the 6-aryl-4-amino-picolinate compounds of Formula I directly as herbicides, it is preferable to use them in mixtures containing a herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calciumdodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims. Many of the starting materials useful for the preparation of the compounds of the present invention, e.g., 4-amino-3,6-dichloropyridine-2-carboxylic acid, 4-amino-3,5,6-trifluoro-2-cyanopyridine, methyl 4-amino-6-bromo-3,5-difluorpyridine-2-carboxylate and methyl 4-amino-6-bromo-3-chloropyridine-2-carboxylate, are described in U.S. Pat. No. 6,297,197 B1.

EXAMPLES

1. Preparation of 3-bromo-6-chloro-2-fluorophenol

A solution of 1-bromo-4-chloro-2-fluorobenzene (20.4 g, 0.100 mol) in tetrahydrofuran (THF; 50 mL) was slowly added to lithium diisopropyl amide (LDA; 0.125 mol) in THF (600 mL) at −50° C. After addition the solution was warmed to −20° C. and then cooled to −50° C. and a solution of trimethyl borate (13.5 g, 0.130 mol) in tetrahydrofuran (20 mL) was added slowly and the temperature was warmed to −20° C. The mixture was then cooled to −70° C. and solution of peracetic acid (32% in acetic acid, 0.150 mol) was slowly added and the mixture was warmed to ambient temperature. Water (250 mL) was added and solution extracted with ethyl acetate (2×200 mL). The combined organic phases were dried and concentrated. The black oil was purified by column chromatography (20% ethyl acetate in hexanes) to give 3-bromo-6-chloro-2-fluorophenol (14.1 g, 0.063 mol): $^1$H NMR (CDCl$_3$): δ 7.05 (m, 2H), 5.5 (bs, 1H).

The following compounds were prepared according to the procedure of Example 1.
3-Bromo-2,6-dichlorophenol: mp 69-70° C.
3-Bromo-2-fluoro-6-trifluoromethylphenol: $^1$H NMR (CDCl$_3$): δ 7.20 (m, 2H), 5.85 (bs, 1H).
3-Bromo-2-chloro-6-fluorophenol: LC/MS (m/z=225).

2. Preparation of 1-bromo-4-chloro-2-fluoro-3-methoxybenzene

A heterogeneous mixture of 3-bromo-6-chloro-2-fluorophenol (14.4 g, 0.064 mol), methyl iodide (13.5 g, 0.096 mol) and potassium carbonate (8.8 g, 0.064 mol) in acetonitrile (100 mL) was heated under reflux for 2 hours. The mixture was cooled, diluted with water (100 mL) and extracted with ethyl ether (2×150 mL). The combined extracts were dried and concentrated. The dark oil was purified by chromatography (5% ethyl acetate in hexanes) to give 1-bromo-4-chloro-2-fluoro-3-methoxybenzene (14.8 g, 0.062 mol): $^1$H NMR (CDCl$_3$): δ 7.20 (m, 1H), 7.10 (dd, 1H), 4.0 (s, 3H).

The following compounds were prepared according to the procedure of Example 2.
1-Bromo-4-chloro-3-ethoxy-2-fluorobenzene: $^1$H NMR (CDCl$_3$): δ 7.20 (m, 1H), 7.10 (dd, 1H), 4.20 (q, 2H), 1.50 (t, 3H).
1-Bromo-4-chloro-2-fluoro-3-isopropropoxybenzene: $^1$H NMR (CDCl$_3$): δ 7.20 (m, 1H), 7.10 (dd, 1H), 4.5 (m, 1H), 1.40 (d, 6H).
1-Bromo-4-chloro-2-fluoro-3-(2-methoxyethoxy)benzene: $^1$H NMR (CDCl$_3$): δ 7.25 (m, 1H), 7.15 (dd, 1H), 4.25 (t, 2H), 3.75 (t, 2H), 3.5 (s, 3H).
1-Bromo-2-fluoro-3-methoxy-4-trifluoromethylbenzene: $^1$H NMR (CDCl$_3$): δ 7.39 (d, 1H), 7.21 (d, 1H), 6.18 (tt, 1H), 4.24 (td, 2H).
1-Bromo-2,4-dichloro-3-ethoxybenzene: $^1$H NMR (CDCl$_3$): δ 7.32 (d, 1H), 7.17 (d, 1H), 4.10 (q, 2H), 1.47 (t, 3H).
1-Bromo-2,4-dichloro-3-methoxybenzene: $^1$H NMR (CDCl$_3$): δ 7.35 (d, 1H), 7.15 (d, 1H), 3.95 (s, 3H).
1-Chloro-3,5-difluoro-2-methoxybenzene: GC-MS (m/z=178).
1-Chloro-3,5-difluoro-2-ethoxybenzene: GC-MS (m/z=192) bp 80-85°/30 mm.
1,3-Dichloro-5-fluoro-2-methoxybenzene: GC-MS (m/z=194).
1-Bromo-3-butoxy-4-chloro-2-fluorobenzene: GC-PCI (m/z=180).
1-Bromo-4-chloro-2-fluoro-3-methoxymethoxybenzene: GC-MS (m/z=269).
1-Bromo-2-chloro-4-fluoro-3-methoxybenzene: GC-MS (m/z=239).
3-Chloro-5-fluoro-2-methoxybenzaldehyde: GC-MS (m/z=188).
1,3-Difluoro-3-ethoxybenzene: GC-MS (m/z=158).

3. Preparation of 1-bromo-4-chloro-2-fluoro-5-methoxybenzene

A solution of 4-chloro-2-fluoro-5-methoxyaniline (25.0 g, 0.143 mol) in 10% HBr (250 mL) was cooled to 0° C. and a solution of sodium nitrite (15.0 g, 0.218 mol) in water (20 mL) was slowly added. Methylene chloride (50 mL) and curpric bromide (30.0 g, 0.244 mol) were added slowly and then the mixture was warmed to ambient temperature and stirred for 1 hour. The reaction mixture was filtered through a bed of celite and extracted with methylene chloride (2×100 mL) and the combined organic phases were dried (sodium sulfate) and concentrated. Chromatography of the dark oil (5% ethyl acetate in hexanes) gave 1-bromo-4-chloro-2-fluoro-5-methoxybenzene (16.6 g, 0.070 mol): $^1$H NMR (CDCl$_3$): δ 7.20 (m, 1H) 7.05 (dd, 1H), 4.00 (s, 3H).

4. Preparation of 1-bromo-4-chloro-2-fluoro-3-difluoromethoxybenzene

To a solution of 3-bromo-6-chloro-2-fluorophenol (1.00 g, 4.44 mmol) and sodium chlorodifluoroacetate in dimethylformamide (DMF; 9 mL) was added potassium carbonate (1.22 g, 5.32 mmol) and water (1.77 mL) and the resulting mixture heated to 100° C. for 4 hours. The solution was cooled to ambient temperature and concentrated hydrochloric acid (2.5 mL) and water (4 mL) were added and stirred at ambient temperature overnight. The solution was cooled in an ice bath and neutralized with 2N sodium hydroxide and then extracted with ethyl ether (2×25 mL). The combined extracts were washed with brine, dried (sodium sulfate), and concentrated to give 1-bromo-4-chloro-2-fluoro-3-difluoromethoxybenzene (1.20 g, 4.2 mmol). This material was used without further purification.

5. Preparation of 1-bromo-4-chloro-3-(2,2-difluoroethoxy)-2-fluorobenzene

A solution of 3-bromo-6-chloro-2-fluorophenol (15.4 g, 0.068 mol) in DMF (25 mL) was slowly added to a suspension of sodium hydride (60% dispersion in mineral oil) (4.0 g, 0.10 mol) in DMF (100 mL) and the mixture was stirred 1 hour. A solution of methanesulfonic acid 2,2 difluoroethyl ester (17.5 g, 0.109 mol) in DMF (10 mL) was slowly added. The resulting solution was heated to 70° C. for 18 hours. The solution was diluted with water (200 mL) and extracted with ethyl ether. The combined organic phases were dried (sodium sulfate) and concentrated. The residual oil was purified by chromatography (in hexanes) to give 1-bromo-4-chloro-3-(2,2-difluoroethoxy)-2-fluorobenzene (9.0 g, 0.031 mol): $^1$H NMR (CDCl$_3$): δ 7.3 (m, 1H), 7.10 (dd, 1H), 6.15 (dt, 1H), 4.35 (m, 2H).

The following compound was prepared according to the procedure of Example 5.

1-Bromo-2,4-dichloro-3-(2,2-difluoroethoxy)benzene: $^1$H NMR (CDCl$_3$): δ 7.35 (m, 1H), 7.15 (dd, 1H), 6.15 (tt, 1H), 4.35 (dt, 2H).

6. Preparation of 1-bromo-4-chloro-2-fluoro-3-(methylthio)benzene

A solution of 1-bromo-4-chloro-2-fluorobenzene (20.4 g, 0.100 mol) in THF (50 mL) was slowly added to LDA (0.125 mol) in THF (600 mL) at −50° C. After addition, the solution was warmed to −20° C. and then cooled to −50° C. and a solution of dimethyldisulfide (18.8 g, 0.20 mol) in THF (50 mL) was slowly added and the mixture was warmed to ambient temperature. The reaction was quenched with water (200 mL) and extracted with ethyl acetate (2×150 mL) and the combined organic phases dried (sodium sulfate) and concentrated. The residual red oil was purified by chromatography (5% ethyl acetate in hexanes) to give 1-bromo-4-chloro-2-fluoro-3-(methylthio)benzene (23.9 g, 0.094 mol): $^1$H NMR (CDCl$_3$): δ 7.40 (m, 1H), 7.15 (dd, 1H), 2.50 (s, 3H).

The following compound was prepared according to the procedure of Example 6.

1-Bromo-2,4-dichloro-3-(methylthio)benzene: $^1$H NMR (CDCl$_3$): δ 7.52 (d, 1H), 7.25 (d, 1H), 2.46 (s, 3H).

7. Preparation of 3-bromo-6-chloro-2-fluorobenzaldehyde

A solution of 1-bromo-4-chloro-2-fluorobenzene (20.4 g, 0.100 mol) in THF (50 mL) was slowly added to LDA (0.125 mol) in THF (600 mL) at −50° C. After addition the solution was warmed to −20° C. and then cooled to −50° C. and a solution of DMF (14.6 g, 0.20 mol) in THF (50 mL) was slowly added and the reaction mixture was warmed to ambient temperature. The reaction was quenched with water (250 mL) and extracted with ethyl acetate (2×150 mL) and the combined organic phases were dried (sodium sulfate) and concentrated. The solid residue was recrystallized from hexane to give 3-bromo-6-chloro-2-fluorobenzaldehyde (40.0 g, 0.169 mol): mp 92-93° C.

The following compounds were prepared according the procedure of Example 7 by quenching with appropriate electrophile, e.g., an aldehyde, ester or ketone.

1-(3-Bromo-6-chloro-2-fluorophenyl)-1-ethanol): $^1$H NMR (CDCl$_3$): δ 7.40 (m, 1H), 7.15 (m, 1H), 5.40 (m. 1H), 2.50 (m, 1H), 1.85 (d,3H).

3-Bromo-2,4-dichlorobenzaldehyde: mp 96-97° C.

1-(3-Bromo-2,6-dichlorophenyl)-1-ethanol): $^1$H NMR (CDCl$_3$): δ 7.60 (d, 1H), 7.15 (d, 1H), 5.45 (m, 1H), 3.0 (d, 1H), 1.85 (d,3H).

1-Bromo-4-chloro-3-ethyl-2-fluorobenzene: GC/PCI (m/z=236).

1-(3-Bromo-6-chloro-2-fluorophenyl)-2,2,2-trifluoroethanone: GC/PCI (m/z=304).

1-(3-Bromo-6-chloro-2-fluorophenyl)-1-propanol): $^1$H NMR (CDCl$_3$): δ 7.40 (m, 1H), 7.15 (m, 1H), 5.40 (m. 1H), 2.50 (m, 1H), 1.90 (m, 4H). 1.00 (t, 3H).

2-(3-Bromo-6-chloro-2-fluorophenyl)-2-propanol): $^1$H NMR (CDCl$_3$): δ 7.40 (m, 1H), 7.15 (m, 1H), 3.45 (s, 1H), 1.80 (m, 6H).

8. Preparation of 3-chloro-5-fluoro-2-hydroxybenzaldehyde

A solution of 2-chloro-4-fluorophenol (15.0 g, 102 mmol) in 150 g of 50% sodium hydroxide, water (30 mL) and chloroform (45 mL) were heated under reflux for 8 hours, additional chloroform (45 mL) was added every 2 hours. The mixture was then cooled and allowed to stand for 18 hours and the precipitated sodium salt was collected. The solid was slurried in water (200 mL) and the pH adjusted to 1.5 with 6N hydrochloric acid and then extracted with ethyl acetate (2×100 mL). The combined extracts were washed with brine, dried and concentrated. The residue was purified by chromatography (1:1 methylene chloride:hexanes) to give 3-chloro-5-fluoro-2-hydroxybenzaldehyde (5.0 g, 29 mmol): LC/MS (m/z=174).

9. Preparation of 1-bromo-4-chloro-2-fluoro-3-difluoromethylbenzene

Diethylamino sulfur trifluoride (15.3 g, 0.096 mol) was added slowly to a solution of 3-bromo-6-chloro-2-fluorobenzaldehyde (7.50 g, 0.032 mol) in methylene chloride at 0° C. and the mixture stirred for 1 hour after allowing to warm to ambient temperature. The reaction was carefully quenched with a saturated solution of sodium bicarbonate in water (100 mL) and extracted with methylene chloride (2×75 mL) and the combined extracts dried (sodium sulfate) and concentrated to give 1-bromo-4-chloro-2-fluoro-3-difluoromethylbenzene (7.20 g, 0.028 mol): $^1$H NMR (CDCl$_3$): δ 7.60 (m, 1H), 7.05 (m, 1H), 7.00 (d, 1H).

The following compounds were prepared according to the procedure in Example 9.

1-Bromo-2,4-dichloro-3-difluoromethylbenzene: LC/MS ESI (m/z=271).

1-Difluoromethyl-3-fluoro-4-iodo-2-methoxybenzene: LC/MS (m/z=302).

2-Chloro-4-difluoromethyl-3-methoxy-1-nitrobenzene: LC/MS (m/z=237) (used without complete purification.

3-Chloro-1-difluoromethyl-2-methoxybenzene: LC/MS (m/z=210).

10. Preparation of 2-chloro-4-difluoromethyl-3-methoxyaniline

A solution of crude 2-chloro-4-difluoromethyl-3-methoxy-1-nitro-benzene in ethanol (50 mL) containing 5% palladium on charcoal (250 mg) was hydrogenated (50 psi) for 5 hours. The solution was filtered and concentrated to give 2-chloro-4-difluoromethyl-3-methoxyaniline (1.3 g, 48 mmol): LC/MS (m/z=207).

11. Preparation of N-pivaloyl-2-bromo-4-chloro-3-methoxyaniline

To solution of N-pivaloyl-4-chloro-3-methoxyaniline (5.0 g, 21 mmol) in tetrahydrofuran (60 mL) at −60° C. was added n-butyl lithium (2.5M, 44 mmol). The solution was allowed to warm to 0° C. and stir for 3 hours. Ethylene dibromide (9.9 g, 53 mmol) was added and the solution stirred for 18 hours before being quenched with ammonium chloride (saturated solution, 20 mL) and extracted with ethyl ether (2×50 mL). The combined extracts were washed with brine, dried (sodium sulfate) and concentrated. The residue was purified by chromatography (10% ethyl acetate/hexanes) to give N-pivaloyl-2-bromo-4-chloro-3-methoxyaniline (3.7 g, 1.2 mmol): LC/MS (m/z=320).

12. Preparation of 2-bromo-4-chloro-1-iodo-3-methoxybenzene

A solution of N-pivaloyl-2-bromo-4-chloro-3-methoxyaniline (3.7 g, 1.2 mmol) in dioxane (35 mL) was treated with concentrated hydrochloric acid (35 mL) and the solution heated under reflux for 2 hours. After the solution was cooled the pH was adjusted to 10 by addition of sodium hyrdroxide (50% solution) and extracted with ethyl ether (2×50 mL). The combined extracts were washed with brine, dried (sodium sulfate) and concentrated. The crude aniline was dissolved in 2N hydrochloric acid and sodium nitrite (750 mg, 11 mmol) was added and the solution stirred for 20 minutes. This solution was poured into a vigorously stirred solution of sodium iodide (3.3 g, 22 mmol) in water (20 mL) and methylene chloride (30 mL) and stirred for 20 minutes. The solution was then extracted with methylene chloride (2×25 mL) and the combined extracts washed with brine, dried (sodium sulfate) and concentrated. The residue was purified by chromatography (hexanes) to give 2-bromo-4-chloro-1-iodo-3-methoxybenzene (1.5 g, 0.6 mmol): LC/MS (m/z=267).

The following compounds were prepared according to the procedure of Example 12.

4-Chloro-2,6-difluoro-5-methyl-1-iodobenzene: bp 60-70° C./0.75 mm.

2-Chloro-4-difluoromethyl-3-methoxy-1-iodobenzene: LC/MS (m/z=318).

1-chloro-2-difluoromethyl-3,5-difluoro-4-iodobenzene: LC/MS (m/z=324).

13. Preparation of 3-chloro-2-methoxy-4-nitrotoluene

A solution of 4-nitro-2-hydroxytoluene (5.0 g, 33 mmol) in chloroform (40 mL) was heated under reflux and treated with a stream of chlorine for 1 hour. Upon cooling, the solution was washed with sodium bicarbonate (saturated solution), brine, dried (sodium sulfate) and concentrated. The residue was dissolved in acetonitrile (75 mL), treated with potassium carbonate (9.1 g, 66 mmol) and iodomethane (2.5 ml, 5.7 g, 40 mmol) and heated under reflux for 2 hours. Upon cooling, the solution was concentrated and the residue was taken up in ethyl ether (75 mL) and washed with water (50 mL), brine, dried (sodium sulfate) and concentrated. The crude product was purified by chromatography on silica with 1-5% ethyl acetate/hexane to 3-chloro-2-methoxy-4-nitrotoluene (3.0 g, 15 mmol): LC/MS (m/z=201).

14. Preparation of 3-chloro-2-methoxy-4-nitrobenzaldehyde

A solution of 3-chloro-2-methoxy-4-nitrotoluene (1.0 g, 5.0 mmol) in acetic acid (10 mL) and acetic anhydride (10 mL) was cooled to 5° C. and treated with 1 mL conc. $H_2SO_4$. Chromium trioxide (1.4 g, 14 mmol) was added in portions over 10 minutes while the reaction temperature was maintained at 0-5° C. After 30 minutes at this temperature, the mixture was poured onto ice-water (20 g) and the mixture was extracted with ethyl acetate (2×25 mL). The combined organic phases were washed with brine, dried (sodium sulfate) and concentrated. The crude bis-acetate was combined with water (10 mL), ethanol (10 mL) and concentrated sulfuric acid (1 mL) and heated to reflux for 40 minutes. Upon cooling, the mixture was diluted with water (20 mL) and extracted with ethyl acetate (2×50 mL). The combined extracts were washed with brine, dried (sodium sulfate) and concentrated. The crude mixture was chromatographed (10% ethyl acetate/hexanes) to give 3-chloro-2-methoxy-4-nitrobenzaldehyde (400 mg, 1.9 mmol): LC/MS (m/z=215).

15. Preparation of (3-bromo-6-chloro-2-fluorophenyl)methanol

To a solution of 3-bromo-6-chloro-2-fluorobenzaldehyde (20.0 g, 0.084 mol) in ethanol (250 mL) was added sodium borohydride (6.4 g, 0.168 mol) and the reaction mixture was stirred at ambient temperature for 1 hour. The mixture was diluted with water (300 mL) and extracted with ethyl acetate (2×200 mL), dried (sodium sulfate) and concentrated. The crude solid was recrystallized from hexanes to give (3-bromo-6-chloro-2-fluorophenyl) methanol (10.4 g, 0.043 mol): $^1$H NMR (CDCl$_3$): δ 7.50 (m, 1H), 7.15 (dt, 1H), 4.90 (s, 2H), 2.10 (bs, 1H).

The following compounds were prepared according to the procedure of Example 15.

1-(3-Bromo-6-chloro-2-fluorophenyl)-2,2,2-trifluoroethanol: GC/PCI (m/z=306).

3-Fluoro-4-iodo-2-methoxyphenyl)methanol: LC/MS (m/z=282).

16. Preparation of 1-bromo-4-chloro-3-fluoromethyl-2-fluorobenzene

A solution of diethylamino sulfur trifluoride (7.6 g, 0.047 mol) in methylene chloride (25 mL) was slowly added to (3-bromo-6-chloro-2-fluorophenyl) methanol (10.3 g, 0.043 mol) in methylene chloride (150 mL) at 0° C. The solution was stirred at ambient temperature for 1 hour. A saturated solution of sodium bicarbonate (100 mL) was cautiously added and the mixture extracted with methylene chloride (2×100 mL). The combined organic phases were dried (sodium sulfate) and concentrated. The dark residual oil was purified by chromatography (5% ethyl acetate in hexanes) to give 1-bromo-4-chloro-3-fluoromethyl-2-fluorobenzene (6.20 g, 0.024 mol): $^1$H NMR (CDCl$_3$): δ 7.55(m, 1H) 7.18 (dd, 1H) 5.6 (d, 2H).

The following compounds were prepared according to the procedure in Example 16.

1-Bromo-4-chloro-2-fluoro-3-(1-fluoro-1-methylethyl)benzene: $^1$H NMR (CDCl$_3$): δ 7.42 (m, 1H), 7.10 (m, 1H), 6.05 (dq, 1H) 1.95 (dd, 6H).

1-Bromo-2,4-dichloro-3-(1-fluoroethyl)benzene: GC/PCI (m/z=270).

1-Bromo-4-chloro-2-fluoro-3-(1-fluoroethyl)benzene: GC/PCI (m/z=255).

1-Bromo-4-chloro-2-fluoro-3-(1,2,2,2-tetrafluoroethyl)benzene: GC/EI (m/z=308).

1-Bromo-4-chloro-2-fluoro-3-(1-fluoropropyl)benzene: GC/EI (m/z=267).

2-Fluoro-4-fluoromethyl-1-iodo-3-methoxybenzene: LC/MS (m/z=284).

17. Preparation of 1-bromo-4-chloro-2-fluoro-3-methoxymethylbenzene

A solution of 1-bromo-4-chloro-2-fluorobenzene (20.4 g, 0.100 mol) in THF (50 mL) was slowly added to LDA (0.125 mol) in THF (600 mL) at −50° C. After addition the solution was warmed to −20° C. and then cooled to −50° C. a solution of bromomethoxymethane (25 g, 0.200 mol) in THF (25 mL) was slowly added and the reaction mixture was warmed to ambient temperature. The reaction was quenched with water (400 mL) and extracted with diethyl ether (2×150 mL). The combined organic phases were dried (sodium sulfate) and concentrated. The residual oil was distilled (70°-75° C./0.5 mm) to give 1-bromo-4-chloro-2-fluoro-3-methoxymethylbenzene (18.0 g, 0.071 mol): $^1$H NMR (CDCl$_3$): δ 7.50 (m, 1H), 7.15 (dd, 1H), 4.65 (s, 1H), 3.40 (s, 1H).

The following compound was prepared according to the procedure of Example 17.

1-Bromo-4-chloro-2-fluoro-3-methylbenzene: $^1$H NMR (CDCl$_3$): δ 7.30 (m, 1H), 7.05 (dd, 1H), 2.35 (s, 3H).

18. Preparation of 2-(4-chloro-2-fluoro-3-methoxyphenyl)-[1,3,2]-dioxaborinane To a solution of 1-bromo-4-chloro-2-fluoro-3-methoxybenzene (10.4 g, 0.043 mol) in diethyl ether (150 mL) at −78° C. was slowly added n-butyl lithium (2.5M, 19.0 mL, 0.0475 mol) and the solution was stirred for 30 minutes. A solution of triisopropyl borate (12.0 g, 0.064 ml) in THF (25 mL) was slowly added and the solution was warmed to a 0° C. Acetyl chloride (10.0 g, 0.13 mol) was added. After stirring for 1 hour, the solution was concentrated and the solid residue taken into ethyl acetate (150 mL) and a 1N solution of sodium hydroxide (50 mL). Ice was added to the aqueous phase which was then acidified with sufficient concentrated hydrochloric acid to obtain a pH of 2. The heterogeneous mixture was extracted with ethyl acetate (2×150 mL) and the combined organic phases dried (sodium sulfate) and concentrated. The resulting solid was slurried in toluene and propane-1,3-diol (6.6 g, 0.09 mol) was added and the mixture heated under reflux with water being removed with a Dean-Stark trap. After 2 hours the mixture was cooled and concentrated. The resulting oil was taken into methylene chloride (50 mL) and washed with water (25 mL), then dried (sodium sulfate) and concentrated to give 2-(4-chloro-2-fluoro-3-methoxyphenyl)-[1,3,2]-dioxaborinane (6.4 g, 0.062 mol): $^1$H NMR (CDCl$_3$): δ 7.15 (m, 1H), 6.95 (dd, 1H), 4.05 (t, 4H), 3.8 (s, 3H), 1.95 (t, 2H).

The following compounds were prepared according to the procedure of Example 18.

2-(4-Chloro-2-fluoro-5-methoxyphenyl)-[1,3,2]-dioxaborinane: $^1$H NMR (CDCl$_3$): δ 7.25 (d, 1H), 7.05 (d, 1H), 4.20 (t, 4H), 4.15 (s, 3H), 2.10 (t, 2H).

2-(4-Chloro-2-fluoro-3-ethoxyphenyl)-[1,3,2]-dioxaborinane: $^1$H NMR (CDCl$_3$): δ 7.30 (m, 1H), 7.05 (dd, 1H), 4.20 (m, 7H), 2.05 (t, 3H), 1.50 (t, 3H).

2-(4-Chloro-2-fluoro-3-(methylthio)phenyl)-[1,3,2]-dioxaborinane: $^1$H NMR (CDCl$_3$): δ 7.50 (m, 1H), 7.18 (dd, 1H), 4.20 (t, 4H), 2.50 (s, 3H), 2.05 (t, 2H).

2-(4-Chloro-2-fluoro-3-methoxymethylphenyl)-[1,3,2]-dioxaborinane: $^1$H NMR (CDCl$_3$): δ 7.6 (dt, 1H), 7.25 (dd, 1H), 4.76 (s, 2H), 4.20 (t, 4H), 3.40 (s, 3H), 2.05 (t, 2H).

2-(4-Chloro-2-fluoro-3-isopropoxyphenyl)-[1,3,2]-dioxaborinane: $^1$H NMR (CDCl$_3$): δ 7.25 (m, 1H), 7.15 (dd, 1H), 4.5 (q, 1H), 4.20 (t, 4H), 2.05 (t, 2H), 1.50 (d, 6H).

2-(4-Chloro-2-fluoro-3-difluoromethylphenyl)-[1,3,2]-dioxaborinane $^1$H NMR (CDCl$_3$): δ 7.75 (m, 1H), 7.15 (dd, 1H), 6.90-7.15 (t, 1H) 4.20 (t, 4H), 2.05 (t, 2H).

2-(4-Chloro-2-fluoro-3-fluoromethylphenyl)-[1,3,2]-dioxaborinane $^1$H NMR (CDCl$_3$): δ 7.70 (m, 1H), 7.25 (dd, 1H), 5.8 (d, 2H), 4.20 (t, 4H), 2.05 (t, 2H).

4-[1,3,2]-Dioxaborinan-2-yl-3-fluoro-2-methoxybenzonitrile: $^1$H NMR (CDCl$_3$): δ 7.40 (m, 1H), 7.3 (dd, 1H), 4.25 (t, 4H), 4.15 (s, 3H), 2.10 (t, 3H).

2-(4-Chloro-2-fluoro-3-methoxyethoxyphenyl)-[1,3,2]-dioxaborinane: $^1$H NMR (CDCl$_3$): δ 7.35 (m, 1H), 7.15 (dd, 1H), 4.25 (m, 6H), 3.75 (d, 2H), 3.48 (s, 3H), 2.15 (t, 3H).

2-(2,4-Dichloro-3-ethoxyphenyl)-[1,3,2]-dioxaborinane: $^1$H NMR (DMSO-d$_6$): δ 7.40 (d, 1H), 7.29 (d, 1H), 4.08 (m, 4H), 4.00 (q, 2H), 1.99 (m, 2H), 1.34 (t, 3H).

2-[4-Chloro-2-fluoro-3-(2,2-difluoroethoxyphenyl]-[1,3,2]-dioxaborinane: $^1$H NMR (CDCl$_3$): δ 7.45 (m, 1H), 7.15 (dd, 1H), 6.15 (tt, 1H), 4.38 (t, 4H), 4.20 (t, 2H), 2.10 (t, 2H).

2-(4-Chloro-2-fluoro-5-ethoxyphenyl)-[1,3,2]-dioxaborinane: $^1$H NMR (CDCl$_3$): δ 7.25 (d, 1H), 7.05 (d, 1H), 4.20 (t, 4H), 4.15 (t, 2H), 2.10 (t, 2H), 1.45 (t, 3H).

2-(2,4-Dichloro-3-(methylthio)phenyl)-[1,3,2]-dioxaborinane: $^1$H NMR (CDCl$_3$): δ 7.45-7.28 (m, 2H), 3.86 (m, 4H), 2.42 (s, 3H), 1.80 (m, 2H).

6-Chloro-3-[1,3,2]-dioxaborinan-2-yl-2-fluorobenzonitrile: $^1$H NMR (CDCl$_3$): δ 7.85 (m, 1H), 6.25 (m, 1H), 4.20 (m, 4H), 2.10 (m, 2H).

19. Preparation of 1-fluoro-2,3-methylenedioxybenzene

Aliquot 336 (methyltrioctylammonium chloride, 0.63 g, 1.6 mmol), dibromomethane (40.7 g, 234.2 mmol) and water (31 mL) were placed in a 500 mL 3-necked flask equipped with an addition funnel, condenser and a stir bar. The addition funnel was charged with a solution of 3-fluorocatechol (20.0 g, 160 mmol) in 5M sodium hydroxide (80 mL). The mixture in the flask was heated to reflux and the solution of the catechol was added dropwise with good stirring over 2 hours and the resulting dark mixture heated an additional 2 hours at reflux. After cooling to room temperature, the reaction was diluted with methylene chloride and the layers separated. The aqueous layer was extracted with methylene chloride and the combined organic layers dried (Na$_2$SO$_4$ with charcoal). Filtration and concentration to a constant weight on the rota-vap gave 1-fluoro-2,3-methylenedioxybenzene (14.6 g, 104.2 mmol) as a dark yellow oil: $^1$H NMR (CDCl$_3$): 6.80 (m, 1H), 6.68 (m, 2H), 6.04 (s, 2H).

20. Preparation of 2-fluoro-3,4-methylenedioxyphenylboronic acid

1-Fluoro-2,3-methylenedioxybenzene (5.0 g, 35.7 mmol) was dissolved in THF (70 mL) and the solution cooled to −65° C. in a dry ice acetone bath. n-Butyl lithium (2.5 g, 15.7 mL, 39.3 mmol) was added to the solution via syringe with stirring. The reaction was allowed to warm to −35° C. over 1 hour then re-cooled to −65° C. and treated with trimethylborate (4.1 g, 39.3 mmol) via syringe. The reaction was allowed to warm slowly to room temperature then quenched with 1N HCl (50 mL), stirred for 15 minutes then diluted with ether and the layers separated. The organic layer was extracted with 1N sodium hydroxide and this extract separated from the ether and acidified with 1N hydrochloric acid. The acidic aqueous layer was extracted with two portions of ether and these combined ether extracts were dried (sodium sulfate), filtered and concentrated to a oily solid which was triturated with methylene dichloride. The resulting solid was collected by filtration, washed with methylene dichloride and dried to give 1-fluoro-2,3-methylenedioxyphenylboronic acid (1.4 g, 7.6 mmol) as a tan solid: $^1$H NMR (DMSO-d$_6$): δ 8.05 (bs, 2H), 7.08 (dd, 1H), 6.76 (d, 1H), 6.08 (s, 2H).

The following compounds were prepared according to the procedure in Example 20.

2-Fluoro-3-methoxy-4-methylphenylboronic acid: $^1$H NMR (300 MHz, d$_6$-DMSO+H$_2$O): δ 7.32 (bs, 2H), 7.11 (dd, 1H, J=7.2, 5.7 Hz), 6.92 (d, 1H, J=7.2 Hz), 3.74 (s, 3H), 2.19 (s, 3H).

4-Bromo-2-fluoro-3-methoxyphenylboronic acid: $^1$H NMR (300 MHz, DMSO d$_6$+D$_2$O): δ 8.36 (bs, 2H), 7.38 (dd, 1H, J=8.4), 7.17 (dd, 1H,), 3.82 (d, 3H,).

21. Preparation of 2-(2-fluoro-3,4-methylenedioxyphenyl)-[1,3,2]-dioxaborinane 2-Fluoro-3,4-methylenedioxyphenylboronic acid (1.4 g, 7.6 mmol) was slurried in toluene and propane-1,3-diol (0.6 g, 7.9 mmol) and the mixture heated under reflux for 0.5 hour. The mixture was cooled, filtered through glass wool and concentrated to give 2-(2-fluoro-3,4-methylenedioxyphenyl)-[1,3,2]-dioxaborinane (1.6 g, 7.1 mmol): $^1$H NMR (DMSO-d$_6$): δ 7.12 (dd, 1H, J=7.8, 5.7 Hz), 6.75 (d, 1H), 6.09 (s, 2H), 4.06 (t, 4H), 1.98 (m, 2H).

22. Preparation of 3-bromo-6-chloro-2-fluorobenzonitrile

A suspension of 3-bromo-6-chloro-2-fluorobenzaldehyde (9.0 g, 0.04 mol) and O-sulfinic acid hyrdroxyamine (7.50 g, 0.07 mole) in water (300 mL) was warmed to 50° C. for 18 hours. The suspension was cooled and the solid collected to give 3-bromo-6-chloro-2-fluorobenzonitrile (8.8 g, 0.04 mol): $^1$H NMR (CDCl$_3$): δ 7.75 (m, 1H), 7.25 (m, 1H).

23. Preparation of 3-bromo-2-fluoro-6-chlorobenzamide

Concentrated sulfuric acid (15 mL) was placed in a 100 mL 3-neck flask equipped with an internal thermometer and then heated to 55° C. 3-Bromo-2-fluoro-6-chlorobenzonitrile (11.0 g, 47 mmol) was added portion-wise to the acid with stirring maintaining the temperature above 50° C. The dark solution was heated at 65° C. for 24 hours then cooled to room temperature and poured over ice and cautiously neutralized with concentrated ammonium hydroxide. The mixture was extracted with two portions of ethyl acetate and the combined organic layers dried over Na$_2$SO$_4$ (with charcoal). Filtration and concentration gave 3-bromo-2-fluoro-6-chlorobenzamide (11.5 g, 45.5 mmol) as a light orange solid: mp 157-158° C., $^1$H NMR (CDCl$_3$): δ 7.54 (t, 1H), 7.14 (dd, 1H), 6.03 (bs, 1H) 5.81 (bs, 1H).

24. Preparation of 3-bromo-2,6-dichlorobenzamide

3-Bromo-2,6-dichlorobenzoic acid (7.2 g, 26.7 mmol) was treated with thionyl chloride (30 mL, 400.0 mmol) in a 250 mL round bottom flask and the mixture was heated to reflux for 1 hour then cooled to room temperature. Approximately one third of the light yellow solution was removed and concentrated in vacuo. The residue was dissolved in THF (16 mL) and treated with concentrated ammonium hydroxide (6 mL) with good stirring. The mixture was partitioned between ethyl acetate and saturated NaHCO$_3$ and the layers separated and the organics dried over Na$_2$SO$_4$. Filtration and concentration gave 3-Bromo-2,6-dichlorobenzamide (2.19 g) as a foam: mp 117-119° C., $^1$H NMR (300 MHz, d$_6$-DMSO): δ 8.10 (bs, 1H), 7.88 (bs, 1H), 7.79 (d, 1H, J=8.), 7.44 (d, 1H).

25. Preparation of 3-bromo-6-chloro-2-fluoroaniline

Sodium hydroxide (4.0 g, 100.0 mmol) was dissolved in water (70 mL) in a 250 mL round bottomed flask and the resulting solution cooled in an ice bath and treated with bromine (4.7 g, 29.7 mmol) to give a yellow solution. 3-Bromo-2-fluoro-6-chlorobenzenecarboxamide (5.0 g, 19.9 mmol) was added as a solid, slowly with good stirring and the orange mixture was heated to reflux for 2 hours. The cooled reaction mixture was diluted with methylene dichloride and the layers separated and the methylene dichloride dried (Na$_2$SO$_4$). Crystallization of the concentrated filtrate from cold hexanes gave 3-bromo-6-chloro-2-fluoroaniline (2.8 g, 12.6 mmol) as a off white solid: mp 61-62° C., $^1$H NMR (CDCl$_3$): δ 6.94 (dd, 1H), 6.83 (dd, 1H), 4.16 (bs, 2H).

The following compound was prepared according to the procedure in Example 25.
3-Bromo-2,6-dichloroaniline: mp 71-72° C.

26. Preparation of N-(3-bromo-6-chloro-2-fluorophenyl)-N,N-dimethylamine

3-Bromo-6-chloro-2-fluoroaniline (2.5 g, 11.1 mmol) was dissolved in THF (25 mL) in a nitrogen flushed 250 mL round bottomed flask and treated with 37% formaldehyde (0.84 g, 2.1 mL, 27.8 mmol), dibutyl tin dichloride (0.07 g, 0.22 mmol) and phenyl silane (1.33 g, 12.3 mmol) and allowed to stir at room temperature under nitrogen for 48 hours. The reaction mixture was concentrated in vacuo and purified by flash silica gel chromatography (hexanes) to give N-(3-bromo-6-chloro-2-fluorophenyl)-N,N-dimethylamine (2.0 g 7.9 mmol) as a oil: $^1$H NMR (CDCl$_3$): δ 7.19 (dd, 1H), 7.04 (dd, 1H), 2.88 (s, 3H), 2.87 (s, 3H).

The following compounds were prepared according to the procedure of Example 26.
N-(3-Bromo-6-chloro-2-fluorophenyl)-N,N-diethylamine: $^1$H NMR (300 MHz, CDCl$_3$): δ 7.24 (dd, 1H), 7.07 (dd, 1H), 3.16 (dd, 4H), 1.01 (t, 6H)).
N-(3-Bromo-2,6-dichlorophenyl)-N,N-dimethylamine: $^1$H NMR (300 MHz, CDCl$_3$): δ 7.33 (d, 1H), 7.13 (d, 1H), 2.88 (s, 6H).
N-(2-Chloro-4,6-difluorophenyl)-N,N-dimethylamine: Colorless oil. $^1$H NMR (300 MHz, CDCl$_3$): δ 6.93 (ddd, 1H), 6.73 (m, 1H), 2.82 (d, 6H).

27. Preparation of N-(3-bromo-2-fluorophenyl), N-methyl amine

3-Bromo-6-chloro-2-fluoroaniline (1.2 g, 5.2 mmol) was dissolved in THF (12 mL) in a 100 mL round bottomed flask and treated with tetra-N-butyl ammonium bromide (0.015 g, 0.05 mmol) and powdered sodium hydroxide (0.83 g, 20.9 mmol) with stirring. After 5 minutes, the dark mixture was treated with dimethyl sulfate (1.3 g, 10.4 mmol) and the mixture heated at 60° C. for 2 hours. Analysis by TLC (hexanes:ethyl acetate/20:1) indicated some starting material remained. Added additional dimethyl sulfate (0.66 g, 5.2 mmol) and continued heating for 1.5 hour then stirred at room temperature overnight. The reaction was partitioned between diethyl ether and water and the layers separated and the aqueous phase extracted with ether. The combined ether layers were washed with water and dried (MgSO$_4$). Filtration, concentration and purification by flash silica gel chromatography (hexanes) gave N-(3-bromo-6-chloro-2-fluorophenyl)-N-methylamine (0.81 g) as a colorless oil: $^1$H NMR (300 MHz, CDCl$_3$): δ 6.93 (dd, 1H, J=8.4), 6.83 (dd, 1H), 4.00(bs, 1H), 3.09 (d, 3H).

28. Preparation of 1,3-difluoro-2-iodo-4-methoxy-5-methylbenzene

A solution of 1,5-difluoro-2-methoxy-3-methylbenzene (0.65 g, 4.1 mmol) in THF (1 mL) was added to LDA (4.3 mmol) in THF (10 mL) at −55° C. and the solution stirred for 45 minutes. Solid iodine (1.15 g, 4.5 mmol) was added and the solution allowed to warm to ambient temperature. The solution was diluted with ethyl acetate and washed with sodium bicarbonate (saturated solution 15 mL) and sodium thiosulfate (saturated solution, 15 mL), dried (sodium sulfate) and concentrated. The residue was purified by chromatography (hexanes) to give 1,3-difluoro-2-iodo-4-methoxy-5-methylbenzene: $^1$H NMR (300 MHz, CDCl$_3$): δ 6.72 (dd, 1H), 3.84 (d, 3H,), 2.26 (s, 3H).

The following compounds were prepared according to the procedure of Example 28.

3,5-Difluoro-4-iodo-2-methoxybenzonitrile: mp 106-110° C.

N-(6-Chloro-2,4-difluoro-3-iodophenyl)-N,N-dimethylamine: $^1$H NMR (300 MHz, CDCl$_3$): δ 6.98 (dd, 1H), 2.82 (d, 6H).

1,3-Dichloro-5-fluoro-4-iodo-2-methoxybenzene: GC-MS (m/z=320).

1,3-Difluoro-2-iodo-4-methoxy-5-methylbenzene: $^1$H NMR (CDCl$_3$): δ 6.72 (dd, 1H), 3.84 (d, 3H), 2.26 (s, 3H).

2,3-Difluoro-4-iodo-benzonitrile: LC/MS (m/z=265).

3-Chloro-1-difluoromethyl-5-fluoro-4-iodo-2-methoxybenzene: LC/MS (m/z=336).

2-Ethoxy-1,3-difluoro-4-iodobenzene: GC-MS (m/z=284).

1,3-Difluoro-2-iodo-4-methoxy-5-methylbenzene: $^1$H NMR (CDCl$_3$): δ 6.72 (dd, 1H), 3.84 (d, 3H), 2.26 (s, 3H).

3,5 Difluoro-4-iodo-2-methoxybenzonitrile: mp. 106-110° C.

(6-Chloro-2,4-difluoro-3-iodophenyl)dimethyl amine: $^1$H NMR (CDCl$_3$): δ 6.98 (dd, 1H), 2.82 (d, 6H).

2,4,6-Trifluoro-3-iodobenzonitrile: LC/MS (m/z=283).

1-Bromo-3,5-difluoro-4-iodo-2-methoxybenzene: LC/MS (m/z=349).

1,3-Dichloro-5-fluoro-4-iodo-2-methoxybenzene: GC-MS (m/z=320).

29. Preparation of 1-chloro-3,5-difluoro-4-iodo-2-methoxybenzene

To a solution of 1-chloro-3,5-difluoro-2-methoxybenzene (2.0 g, 0.01 mol) in THF at −75° C. was added n-butyl lithium (2.5M in hexanes 6.7 mL) and the resulting solution was stirred at −75° C. for 1 hour. A solution of iodine (5.1 g, 0.02 mol) in THF (10 mL) was added and the reaction mixture was allowed to warm to ambient temperature. The reaction mixture was diluted with ethyl ether (50 mL) and aqueous sodium thiosulfate (10%, 50 mL) was added and stirred for 1 hour. After separating the phases, the organic phase was dried (Na$_2$SO$_4$) and concentrated to give 1-chloro-3,5-difluoro-4-iodo-2-methoxybenzene as a white solid: mp 62-64° C.

The following compound was prepared according to the procedure in Example 29.

1-Chloro-2-ethoxy-3,5-difluoro-4-iodobenzene: GC-MS (m/z=178).

30. Preparation of 3-fluoro-4-iodo-2-methoxybenzonitrile

Sodium hydride (60 mg, 2.5 mmol) was slurried in DMF (15 mL) and treated with dry methanol (120 μl, 96 mg, 3.0 mmol). After stirring for 10 minutes at 25° C., the solution was cooled to −25° C. and treated with 2,3-difluoro-4-iodobenzonitrile (500 mg, 1.9 mmol). After 25 minutes, the mixture was quenched by addition of 10% citric acid solution (5 mL) and warmed to 25° C. The mixture was extracted with ethyl ether (2×15 mL), the combined ether phases washed with water (5 mL), brine, dried (sodium sulfate) and evaporated to give 3-fluoro-4-iodo-2-methoxybenzonitrile (500 mg, 1.8 mmol): LC/MS (m/z=277).

31. Preparation of 3-fluoro-4-iodo-2-methoxybenzaldehyde

3-Fluoro-4-iodo-2-methoxybenzonitrile (1.0 g, 3.6 mmol) was dissolved in toluene (7 mL), cooled to 0° C. and treated in portions with 25 wt. % diisobutyl aluminum hydride (DIBAL) in toluene (3.1 ml, 4.7 mmol) After 30 minutes, the reaction was quenched by addition of methanol (5 mL), poured into 1M sulfuric acid (15 mL) and extracted with ethyl acetate (2×15 mL). The combined extracts were washed with water (5 mL), brine, dried (sodium sulfate) and evaporated to give 3-fluoro-4-iodo-2-methoxybenzaldehyde (450 mg, 1.6 mmol): LC/MS (m/z=260).

32. Preparation of 3-chloro-4-iodo-2-methoxyaniline

3-Chloro-2-methoxyaniline (1 g, 6.4 mmol) was dissolved in methylene chloride (10 mL) in a 250 mL round bottomed flask and treated with water (10 mL), NaHCO$_3$ (1.1 g, 12.7 mmol) and iodine (1.61 g, 6.4 mmol) and the resulting mixture heated to reflux for 2 hours by which time TLC (hexanes:ethyl acetate/4:1) indicated nearly complete conversion. The reaction mixture was diluted with ethyl acetate and washed with saturated Na$_2$S$_2$O$_3$. The organic layer was separated and dried (Na$_2$SO$_4$). Filtration, concentration and purification by flash silica gel chromatography (hexanes:ethyl acetate/8:1) gave 0.71 g of a red oil which was identified as a 2.5:1 mixture of the 3-chloro-4-iodo-2-methoxyaniline and starting material: $^1$H NMR (300 MHz, CDCl$_3$) δ 7.36 (d, 1H, J=8.4 Hz), 6.45 (d, 1H, J=8.4 Hz), 4.10 (bs, 2H), 3.82 (s, 3H). Other runs with excess iodine produced similar results. The mixture was combined with a previous run and used as is without further purification.

33. Preparation of 4-chloro-2,6-difluoro-3-methylaniline

A solution of 2,6-difluoro-3-methylaniline (15 g, 105 mmol) in acetic acid (80 mL) was heated to 70° C. and a solution of sulfuryl chloride (16.0 g, 115 mmol) in acetic acid (40 mL) was added dropwise over 20 minutes. The temperature was maintained for 3 hours, then cooled and concentrated. The residue taken into water (100 mL) and the pH was adjusted to 9 with 2N sodium hydroxide and then extracted with methylene chloride (2×75 mL) and the combined extracts washed with brine, dried (sodium sulfate) and concentrated. The residue was distilled to give 4-chloro-2,6-difluoro-3-methylaniline (12.2 g, 69 mmol): bp 55°-65° C./55 mm.

34. Preparation of 1-bromo-3-chloro-4-iodo-2-methoxybenzene

A mixture of 3-chloro-2-methoxy aniline and 3-chloro-4-iodo-2-methoxyaniline (2.8 g, 2.5:1) was dissolved in dioxane (20 mL) and the resulting solution cooled on an ice bath while being treated with 48% HBr (20 mL). The dark purple mixture was then treated with NaNO$_2$ (1.4 g, 19.5 mmol) in water (6 mL) with good stirring. After 10 minutes, CuBr (5.1 g, 35.5 mmol) was added and the mixture was removed from the ice bath and allowed to warm to room temperature and stir for 0.5 hour. The dark purple mixture was diluted with ethyl acetate and water then filtered through celite with ethyl acetate. The layers were separated and the organic layer was washed with saturated sodium sulfite and saturated ammonium chloride and dried (Na₂SO₄). Filtration, concentration and purification by flash silica gel chromatography (hexanes) gave 2.95 g of a colorless oil which was determined to be a 2.3:1 mixture of 1-bromo-3-chloro-2-methoxybenzene and 1-bromo-3-chloro-4-iodo-2-methoxybenzene which was used as is without further purification: $^1$H NMR (300 MHz, CDCl₃): δ 7.49 (d, 1H), 7.19 (d, 1H,), 3.90 (s, 3H).

35. Preparation of 1-chloro-3,5-difluoro-4-trimethylsilyl-benzene

To a solution of 3,5-difluoro-1-chlorobenzene (10.0 g, 67 mmol) and tetramethylethlenediamine (TMEDA; 7.8 g, 67 mmol) in THF (75 mL) at −75° C., was added n-butyl lithium (2.5M, 68 mmol) and the resulting solution stirred for 30 minutes. A solution of trimethylsilyl chloride (7.6 g, 70 mmol) in THF (15 mL) was added and the solution allowed to warm to ambient temperature and stir for 25 hours. Ammonium chloride (saturated solution 15 mL) was added and the mixture extracted with ethyl ether (2×100 mL) and the combined extracts washed with brine, dried (sodium sulfate) and concentrated. The residual oil was distilled to give 1-chloro-3,5-difluoro-4-trimethylsilylbenzene (13.0 g, 60 mmol): bp 70-75° C.

36. Preparation of 6-chloro-2,4-difluoro-3-trimethylsilylbenzaldehyde

A solution of 1-chloro-3,5-difluoro-4-trimethylsilylbenzene (1.5 g, 6.8 mmol) in THF (10 mL) was added to a solution of lithium tetramethylpiperidine (14 mmol) in THF (15 mL) at −75° C. The solution was stirred for 2 hours then DMF (1.5 g, 20 mmol) was added and the solution allowed to warm to ambient temperature. The reaction was quenched with a saturated solution of ammonium chloride (25 mL) and extracted with ethyl ether (2×25 mL) and the combined extracts dried (sodium sulfate) and concentrated. The residue was purified by chromatography (hexanes) to give 6-chloro-2,4-difluoro-3-trimethylsilylbenzaldehyde (1.4 g, 5.6 mmol): LC/MS (m/z=248).

37. Preparation of 6-chloro-2,4-difluoro-3-iodobenzaldehyde

A solution of 6-chloro-2,4-difluoro-3-trimethylsilylbenzaldehyde (600 mg, 2.4 mmol) in methylene chloride (7 mL) was cooled to 0° C. and treated with solution of iodochloride (780 mg, 4.8 mmol) in methylene chloride (10 mL) and stirred at ambient temperature for 2 hours. Additional iodochloride (900 mg) was added and the solution heated under reflux for 40 minutes. The solution was allowed to cool and was washed with sodium bisulfite (15 ml, 5% solution), water (10 mL), and a saturated solution of sodium bicarbonate (10 mL). The organic phase was dried (sodium sulfate) and concentrated to give 6-chloro-2,4-difluoro-3-iodobenzaldehyde (620 mg, 3.9 mmol): LC/MS (m/z=302).

38. Preparation of 1-bromo-2,4-difluoro-5-methoxybenzene

To a solution of 1,3 dibromo-4,6-difluorobenzene (10.0 g, 37 mmol) in THF (50 mL) at −20° C. was added isopropyl magnesium chloride (2.0M in THF, 42 mmol) and the resulting solution warm to 0° C. and stirred for 30 minutes. Trimethylborate (4.7 g, 45 mmol) was added and the mixture stirred at ambient temperature for 1 hour. The solution was recooled to −20° C. and peracetic acid (32%, 50 mmol) was added and the solution was stirred for 30 minutes at ambient temperature. The solution was then quenched with sodium bisulfite (5% solution, 75 mL) and then acidified with 6 N hydrochloric acid and extracted with ethyl ether (2×75 mL). Combined extracts were dried (sodium sulfate) and concentrated. The crude phenol was dissolved in acetonitrile (40 mL) and potassium carbonate (10 g, 74 mmol) and iodomethane (5.7 g, 40 mmol) were added and stirred at ambient temperature for 20 hours. The solution was concentrated and the residue taken into water (50 mL) and extracted with ethyl ether (2×75 mL) and the combined extracts were washed with brine, dried (sodium sulfate), and concentrated. The residue was purified by chromatography (hexanes) to give 1-bromo-2,4-difluoro-5-methoxybenzene (2.0 g, 8.6 mmol): LC/MS (m/z=223).

39. Preparation of 2-chloro-4,6-difluoro-1-iodo-3-methoxybenzene

A solution of 4-chloro-2,6-difluoro-1-iodo-3-methoxybenzene (2.0 g, 6.6 mmol) in THF (7 mL) was added to LDA (8.0 mmol) in THF (15 mL) at −55° C. and the reaction stirred for 2 hours. The solution was diluted with ethyl ether (50 mL) and washed with ammonium chloride (saturated solution 25 mL), brine and then dried (sodium sulfate) and concentrated. The residual oil was purified by reverse phase chromatography (70% acetonitrile in water) to give 2-chloro-4,6-difluoro-1-iodo-3-methoxybenzene (500 mg. 1.7 mmol): LC/MS (m/z=304).

40. Preparation 4-chloro-3-(dimethylamino)-2-fluorophenylboronic acid

N-(3-Bromo-6-chloro-2-fluorophenyl)-N,N-dimethylaniline (0.88 g 3.5 mmol) was dissolved in ether (10 mL) in an oven dried, nitrogen flushed, 50 mL 3-necked flask equipped with a thermometer. The solution was cooled to −60° C. under nitrogen. n-Butyl lithium (0.23 g, 3.6 mmol, 1.45 mL of a 2.5M solution) was added dropwise via syringe keeping the temperature under −55° C. After 0.5 hours, trimethylborate (0.40 g, 0.38 mmol) was added via syringe and the reaction was allowed to warm to room temperature. 1N HCl (3.5 mL) was added and the mixture was stirred for 0.5 hours. The mixture was diluted with water and ether and the ether layer was separated and dried over Na₂SO₄. Filtration and concentration left 0.753 g of a foam which was triturated with hexanes. The resulting solids were collected by filtration and dried to give 4-chloro-3-(dimethylamino)-2-fluorophenylboronic acid (0.5 g, 2.3 mmol) as an off white solid: $^1$H NMR (DMSO-d₆) revealed the solid to be a mixture of what appears to be the boronic acid and anhydrides. The solid was used as is without further purification or characterization.

The following compounds where prepared according the procedure in Example 40.

4-Chloro-3-(diethylamino)-2-fluorophenylboronic acid: $^1$H NMR (300 MHz, DMSO$_{d6}$+D₂O): δ 8.26 (bs, 2H), 7.26 (m, 2H). 3.05 (q, 4H,), 0.91 (t, 6H,)

2,4-Dichloro-3-dimethylaminophenylboronic acid. This material was isolated as an oily mixture of boronic acid and anhydride and used without further purification or characterization.

2-Chloro-4-fluoro-3-methoxyphenylboronic acid (used without purification)

41. Preparation of [3-chloro-2-fluoro-3-(4,4,5,5-tetramethyl-{1,3,2}dixoborolan-2-yl)-phenyl methyl amine N-(3-bromo-6-chloro-2-fluorophenyl)-N-methylamine (0.84 g, 3.5 mmol) was dissolved in DMF (10 mL) in a nitrogen flushed 50 mL 3-neck flask and the resulting solution was purged with nitrogen for 0.5 hour. Bis(pinacolato)diboron (0.98 g, 3.9 mmol), potassium acetate (1.04 g, 10.6 mmol) and [1,1'-bis(diphenylphosphino)ferrocene]dichloropalladium(II) $CH_2Cl_2$ complex (0.14 g, 0.18 mmol) were added all at once and the mixture heated to 110° C. with a nitrogen purge of the head space through 60° C. and then under an open nitrogen atmosphere for 1.5 hours. The reaction mixture was cooled to room temperature and partitioned between ethyl acetate and brine and the layers separated. The aqueous phase was extracted with ethyl acetate and the combined organics washed with brine and dried ($Na_2SO_4$). Filtration, concentration and purification by flash silica gel chromatography (hexanes:ethyl acetate/5:1) gave [3-chloro-2-fluoro-3-(4,4,5,5-tetramethyl-{1,3,2}dixoborolan-2-yl)-phenyl methyl amine (0.85 g): light green solid: $^1$H NMR (300 MHz, $CDCl_3$): δ 7.05 (m, 2H), 3.96 (bs, 1H), 3.06 (d, 3H,), 1.35 (s, 12H).

42. Preparation of 4-amino-3-chloro-6-(4-chloro-2-fluoro-3-thiomethyl)-phenyl)pyridine-2-carboxylic acid methyl ester (Compound 1)

A solution of 4-amino-3,6-dichloropyridine-2-carboxylic acid methyl ester (2.6 g, 0.012 mol), 2-(4-chloro-2-fluoro-3-thiomethylphenyl)-[1,3,2]-dioxaborinane (4.1 g, 0.016 mol), 1,4-bis(diphenylphosphino)butane (0.610 g, 0.0015 mol) and cesium fluoride (6.7 g, 0.045 mol) in acetonitrile (75 mL) were degassed with nitrogen for 15 minutes. Palladium acetate (0.30 g, 0.0015 mol) was added and the mixture heated to reflux for 4 hours. The reaction mixture was quenched with water and extracted with ethyl acetate (2×100 mL) and the combined extracts were dried (sodium sulfate) and concentrated. The residual solid was purified by chromatography (25%-40% ethyl acetate in hexanes) to give 4-amino-3-chloro-6-(4-chloro-2-fluoro-3-thiomethylphenyl)pyridine-2-carboxylic acid methyl ester (2.0 g, 0.005 mol): $^1$H NMR (DMSO-$d_6$): δ 7.78 (t, 1H), 7.50 (d, 1H), 7.25 (s, 1H), 3.95 (s, 3H), 2.50 (s, 3H).

The following compounds were prepared according to the procedure of Example 42 (in some cases the crude boronic acid was used instead of the ester).

4-Amino-3-chloro-6-(4-chloro-3-cyano-2-fluorophenyl)pyridine-2-carboxylic acid methyl ester (Compound 2): mp 189-190° C.

4-Amino-3-chloro-6-(4-chloro-2-fluoro-3-methoxymethylphenyl)pyridine-2-carboxylic acid methyl ester (Compound 3): mp 116-117° C.

4-Amino-3-chloro-6-(4-chloro-2-fluoro-3-difluoromethylphenyl)pyridine-2-carboxylic acid methyl ester (Compound 4): mp 145-146° C.

4-Amino-3-chloro-6-(4-chloro-2-fluoro-3-fluoromethylphenyl)pyridine-2-carboxylic acid methyl ester (Compound 5): $^1$H NMR ($CDCl_3$): δ 8.05 (dt, 1H), 7.25 (d, 1H), 7.15 (s, 1H), 5.65 (dd, 2H), 4.95 (bs, 2H), 4.00 (s, 3H).

4-Amino-3-chloro-6-(4-cyano-2-fluoro-3-methoxyphenyl)pyridine-2-carboxylic acid methyl ester (Compound 6): $^1$H NMR ($CDCl_3$): δ 7.70 (m, 1H), 7.20 (dd, 1H), 7.10 (d, 1H), 4.95 (bs, 2H), 4.00 (s, 3H).

4-Amino-3-chloro-6-(2,4-dichloro-3-ethoxyphenyl)pyridine-2-carboxylic acid methyl ester (Compound 7): mp 132-133° C.

4-Amino-3-chloro-6-[4-chloro-2-fluoro-3-(2,2-difluoroethoxy)phenyl]pyridine-2-carboxylic acid methyl ester (Compound 8): mp 134-136° C.

4-Amino-3-chloro-6-(4-chloro-2-fluoro-5-ethoxyphenyl)pyridine-2-carboxylic acid methyl ester (Compound 9): mp 115-116° C.

4-Amino-3-chloro-6-[2,4-dichloro-3-(2,2-difluoroethoxy)phenyl]pyridine-2-carboxylic acid methyl ester (Compound 10): mp 113-115° C.

4-Amino-3-chloro-6-[4-chloro-2-fluoro-3-(methoxyethoxy)phenyl]pyridine-2-carboxylic acid methyl ester (Compound 11): mp 89-90° C.

4-Amino-3-chloro-5-fluoro-6-(2-fluoro-3,4-methylenedioxyphenyl)pyridine-2-carboxylic acid methyl ester (Compound 12): mp 151-152° C.

4-Amino-3-chloro-6-(2,4-dichloro-3-methylthiophenyl)pyridine-2-carboxylic acid methyl ester (Compound 13): $^1$NMR ($CDCl_3$): δ $^1$H NMR ($CDCl_3$) δ 7.45 (d, 1H), 7.40 (d, 1H), 6.98 (s, 1H), 4.97 (bs, 2H), 3.98 (s, 3H), 2.44 (s, 3H).

4-Amino-3-chloro-5-fluoro-6-(4-chloro-2-fluoro-3-methoxyphenyl)pyridine-2-carboxylic acid methyl ester (Compound 14): mp 172-173° C.

4-Amino-3-chloro-5-fluoro-6-(4-chloro-2-fluoro-5-methoxyphenyl)pyridine-2-carboxylic acid methyl ester (Compound 15): mp 168-169° C.

4-Amino-3-chloro-6-(4-chloro-3-dimethylamino-2-fluorophenyl)pyridine-2-carboxylic acid, methyl ester (Compound 16): mp 104-106° C.

4-Amino-3-chloro-6-[4-chloro-3-(diethylamino)-2-fluorophenyl]pyridine-2-carboxylic acid, methyl ester (Compound 17): mp 120-121° C.

43. Preparation of 4-acetylamino-3-chloro-6-(4-chloro-2-fluoro-5-methoxyphenyl)pyridine-2-carboxylic acid methyl ester (Compound 18)

A solution of 4-acetylamino-3,6-dichloropyridine carboxylic acid methyl ester (4.3 g, 0.016 mol), 2-(4-chloro-2-fluoro-5-methoxyphenyl)-[1,3,2]-dioxaborinane (4.5 g, 0.018 mol), cesium fluoride (3.5 g, 0.025 mol), and 1,4-bis (diphenylphosphino)butane (0.360 g, 0.0016 mol) in acetonitrile (100 mL) was degassed with nitrogen for 15 minutes before palladium acetate (0.180 g, 0.0016 mol) was added and the solution heated under reflux for 18 hours. Water (150 mL) was added and the resulting solid collected and dried to give 4-acetylamino-3-chloro-6-(4-chloro-2-fluoro-5-methoxyphenyl)pyridine-2-carboxylic acid methyl ester (4.5 g, 0.012 mol): mp 180-182° C.

The following compounds were prepared according to the procedure of Example 43.

4-Acetylamino-3-chloro-6-(4-chloro-2-fluoro-3-methylphenyl)pyridine-2-carboxylic acid methyl ester (Compound 19): mp 151-152° C.

4-Acetylamino-3-chloro-6-(4-chloro-2-fluoro-3-methoxyphenyl)pyridine-2-carboxylic acid methyl ester (Compound 20): mp 159-160° C.

4-Acetylamino-3-chloro-6-(4-chloro-2-fluoro-3-ethoxyphenyl)pyridine-2-carboxylic acid methyl ester (Compound 21): $^1$NMR ($CDCl_3$): δ 9.0 (bs, 1H) 8.00 (m, 1H), 7.60 (m, 1H), 7.25 (s, 1H), 4.25 (q, 2H), 4.00 (s, 3H), 2.35 (s, 3H), 1.50 (t, 3H).

4-Acetylamino-3-chloro-6-(2,4-dichloro-3-methoxyphenyl)pyridine-2-carboxylic acid methyl ester (Compound 22): $^1$NMR ($CDCl_3$): δ 8.90 (s, 1H), 8.05 (s, 1H), 7.40 (d, 1H), 7.30 (d, 1H), 4.05 (s, 3H), 3.95 (s, 3H), 2.35 (s, 3H).

4-Acetylamino-3-chloro-6-(2-fluoro-3,4-methylenedioxyphenyl)pyridine-2-carboxylic acid methyl ester: mp 132-134° C.

4-Acetylamino-3-chloro-6-(2,4-dichloro-3-ethoxy-2-fluorophenyl)pyridine-2-carboxylic acid methyl ester: $^1$H NMR (CDCl$_3$): δ 8.86 (s, 1H), 8.00 (bs, 1H), 7.37 (d, 1H), 7.26 (d, 1H), 4.11 (q, 2H), 4.00 (s, 3H), 2.32 (s, 3H), 1.47 (t, 3H).

4-Acetylamino-3-chloro-6-[2,4-dichloro-3-(2,2-difluoroethoxy)phenyl]pyridine-2-carboxylic acid methyl ester: $^1$H NMR (CDCl$_3$): δ 8.81 (s, 1H), 8.10 (bs, 1H), 7.32 (d, 1H), 7.29 (d, 1H), 6.16 (tt, 1H), 4.22 (td, 2H), 3.95 (s, 3H), 2.28 (s, 3H).

44. Preparation of 4-acetylamino-3-chloro-6-(2,4-difluoro-3-methylphenyl)-pyridine-2-carboxylic acid methyl ester (Compound 23)

A solution of 1-bromo-2,4-difluoro-3-methylbenzene (2.10 g, 0.09 mol), 4-acetylamino-3-chloro-6-trimethylstannylpyridine-2-carboxylic acid methyl ester (4.00 g, 0.01 mol), 1,4-bis(diphenylphosphino)butane (0.140 g, 0.0003 mol) and cesium fluoride (4.5 g, 0.03 mol) in acetonitrile (100 mL) was degassed with nitrogen. Palladium acetate (0.70 g, 0.0003 mol) was added the solution heated to reflux for 2 hours. The reaction mixture was filtered through celite and the filtrate diluted with water (200 mL) and then extracted with ethyl acetate (2×150 mL). The combined organic phases were dried and concentrated and the residual solid was purified by chromatography (50% ethyl acetate in hexanes) to give 4-acetylamino-3-chloro-6-(2,4-difluoro-3-methylphenyl)-pyridine-2-carboxylic acid methyl ester (0.800 g, 0.002 mol): mp 152-153° C.

The following compound was prepared according to the procedure of Example 44.

4-Acetylamino-3-chloro-6-(2,4-dichloro-3-methylphenyl)pyridine-2-carboxylic acid methyl ester (Compound 24): mp 172-174° C.

45. Preparation of (2-fluoro-3-methoxy-4-trifluoromethylphenyl)trimethyl stannane Dioxane (28 mL) was added to an oven dried, nitrogen swept 100 mL 3-neck flask equipped with a condenser and a magnetic stirbar and was deaerated with a purge of nitrogen for 15 minutes. Hexamethylditin (5.0 g, 15.3 mmol), and 1-bromo-2-fluoro-3-methoxy-4-(trifluoromethyl)benzene (3.8 g, 13.9 mmol) were added and the purging continued for 5 minutes. 1,4-bis(diphenylphosphino)butane (0.6 g, 1.4 mmol) and palladium acetate (0.3 g, 1.4 mmol) were added and the head space of the reaction vessel purged with nitrogen while heating to reflux with stirring. The reaction was then stirred at reflux under an open nitrogen atmosphere for 6 hours. TLC (hexanes) indicated complete consumption of starting material. The cooled reaction mixture was concentrated and purified by flash silica gel chromatography (hexanes) to give (2-fluoro-3-methoxy-4-trifluoromethylphenyl)trimethyl stannane (3.93 g, 11.0 mmol) as an oil: $^1$H NMR (CDCl$_3$): δ 7.31 (d, 1H), 7.11 (dd, 1H), 3.98 (d, 3H), 0.38 (s, 9H). All signals had appropriate tin satellites.

The following compounds were prepared according to the procedure in Example 45.

(3-Butoxy-4-chloro-2-fluorophenyl)-trimethyl stannane (used without purification).

4-Chloro-2-fluoro-3-(1-fluoro-1-methyl-ethyl)-trimethyl stannane (used without purification).

46. Preparation of 4-acetylamino-3-chloro-6-(2-fluoro-3-methoxy-4-trifluoromethylphenyl)pyridine-2-carboxylic acid methyl ester In an oven dried, nitrogen flushed 100 mL 3 neck flask equipped with a condenser and a magnetic stirbar was dissolved methyl-4-acetamido-3,6-dichloropyridine-2-carboxylate (1.2 g, 4.6 mmol) and (2-fluoro-3-methoxy-4-trifluoromethylphenyl)trimethyl stannane (1.7 g, 4.6 mmol) in acetonitrile (15 mL) and the resulting solution was de-aerated with a purge of nitrogen for 15 minutes. Cesium fluoride (2.1 g, 13.9 mmol), 1,4-bis(diphenylphosphino)butane (0.2 g, 0.46 mmol) and palladium acetate (0.1 g, 0.46 mmol) were added and the head space of the reaction was purged with nitrogen as the reaction was heated to reflux with stirring. The reaction was then stirred under an open nitrogen atmosphere for 5 hours by which time TLC (hexane:ethyl acetate/1:2) indicated complete consumption of starting material. The cooled reaction was filtered through celite with ethyl acetate and the filtrate concentrated and purified by flash silica gel chromatography (hexanes:ethyl acetate/2:1) to give 4-acetylamino-3-chloro-6-(2-fluoro-3-methoxy-4-trifluoromethylphenyl)pyridine-2-carboxylic acid methyl ester (0.19 g, 0.46 mmol) as an oil: $^1$H NMR (CDCl$_3$): δ 9.03 (d, 1H), 8.02 (bs, 1H), 7.68 (bt, 1H), 7.42 (bd, 1H), 4.03 (d, 3H), 4.01 (s, 3H), 2.33 (s, 3H).

The following compounds were prepared according to the procedure in Example 46.

4-Acetylamino-3-chloro-6-(4-chloro-3-butoxy-2-fluorophenyl)pyridine-2-carboxylic acid, methyl ester: LC/MS ESI (m/z=428).

4-Amino-3-chloro-6-[4-chloro-2-fluoro-3-(1-fluoro-1-methylethyl)phenyl]-pyridine-2-carboxlic acid, methyl ester (Compound 25): mp 122-123° C.

47. Preparation of 4-amino-3-chloro-6-(4-chloro-2-fluoro-5-nitrophenyl)-pyridine-2-carboxylic acid methyl ester Methyl 4-amino-3-chloro-6-(4-chloro-2-fluorophenyl)pyridine-2-carboxylate (1.0 g, 3.2 mmol) was added as a solid to well stirred concentrated sulfuric acid (16 mL) at 0° C. Sodium nitrate (0.29 g, 3.5 mmol) was added to the mixture and the resulting yellow solution was stirred at 0° C. for 1.5 hours then diluted with a large quantity of ice and allowed to warm to room temperature. The solution was filtered to remove some solids then the filtrate extracted with 3 portions of ethyl acetate and the combined ethyl acetate layers washed with saturated aqueous NaHCO$_3$ and dried (Na$_2$SO$_4$). Filtration and concentration gave 4-amino-3-chloro-6-(4-chloro-2-fluoro-5-nitrophenyl)pyridine-2-carboxylic acid methyl ester (0.96 g, 2.7 mmol) as a yellow solid: mp 161-163° C.: $^1$H NMR (CDCl$_3$): δ 8.73 (d, 1H), 7.36 (d, 1H), 7.24 (d, 1H), 4.93 (bs, 2H), 4.02 (s, 3H).

48. Preparation of 4-amino-3-chloro-6-(5-amino-4-chloro-2-fluorophenyl)pyridine-2-carboxylic acid methyl ester Iron powder (0.78 g, 13.9 mmol) was added to a slurry of methyl 4-amino-3-chloro-6-(4-chloro-2-fluoro-5-nitrophenyl)pyridine-2-carboxylate (0.5 g, 1.39 mmol) in acetic acid (20 mL) in a 100 mL round bottomed flask. The mixture was heated to 85° C. for 15 minutes. then cooled to room temperature and filtered through celite with ethanol and the filtrate concentrated in vacuo. The residue was partitioned between ethyl acetate and saturated NaHCO$_3$, the layers separated, the aqueous phase extracted with ethyl acetate and the combined organics dried (Na$_2$SO$_4$). Filtration and concentration gave 4-amino-3-chloro-6-(5-amino-4-chloro-2-fluorophenyl)pyridine-2-carboxylic acid methyl ester (0.44 g, 1.33 mmol) as a light brown solid: mp 99-101° C.

49. Preparation of 4-amino-3-chloro-6-(4-chloro-5-dimethylamino-2-fluorophenyl)pyridine-2-carboxylic acid methyl ester (Compound 26)

Methyl 4-amino-3-chloro-6-(5-amino-4-chloro-2-fluorophenyl)pyridine-2-carboxylate (0.38 g, 1.13 mmol)) was dissolved in THF (10 mL) in a nitrogen flushed 250 mL round bottomed flask and treated with 37% formaldehyde (0.068 g, 0.17 mL, 2.27 mmol), dibutyl tin dichloride (0.007 g, 0.023 mmol) and phenyl silane (0.135 g, 1.25 mmol) and allowed to stir at room temperature for 72 hours. The reaction mixture was concentrated in vacuo and purified by flash silica gel chromatography (hexanes:ethyl acetate/2:1) to give 4-amino-3-chloro-6-(4-chloro-5-dimethylamino-2-fluorophenyl)pyridine-2-carboxylic methyl ester (0.283 g 0.8 mmol) as a soft white solid: mp 113-115° C.,
$^1$H NMR (CDCl$_3$): δ 7.66 (d, 1H), 7.14 (d, 1H), 7.14 (d, 1H). 4.91 (bs, 2H), 3.99 (s, 3H), 2.79 (s, 6H).

50. Preparation of 4-acetylamino-3-chloro-6-iodopyridine-2-carboxylic acid, methyl ester To a solution of 4-acetylamino-3-chloro-6-trimethyl-stannanylpyridine-2-carboxylic acid, methyl ester (21.0 g, 54 mmol) in methylene chloride (200 mL) was added iodine (13.7 g, 108 mmol) and the solution was stirred 1 hour at ambient temperature. The solution was filtered through a bed of celite and then washed with sodium thiosulfate (50 mL, 10% solution), dried (sodium sulfate) and concentrated. The residue was purified by chromatography (10% ethyl acetate in hexanes) to give 4-acetylamino-3-chloro-6-iodopyridine-2-carboxylic acid, methyl ester (5.6 g, 18 mmol): GC-MS (m/z=354).

51. Preparation of 4-amino-3-chloro-6-iodopyridine-2-carboxylic acid, methyl ester To solution of 4-acetylamino-3-chloro-6-iodopyridine-2-carboxylic acid, methyl ester (5.0 g, 14 mmol) in methanol (25 mL) was added acetyl chloride (1 mL) and the solution heated under reflux for 1 hour. The solution was cooled and water (25 mL) added and the precipitate was collected. Recrystallization from methanol gave 4-amino-3-chloro-6-iodopyridine-2-carboxylic acid, methyl ester (3.5 g, 11 mmol) mp 152-153° C.

52. Preparation of 4-amino-6-(4-bromo-2-fluoro-3-methoxyphenyl)-3-chloropyridine-2-carboxylic acid methyl ester (Compound 27)

A solution of 4-amino-3-chloro-6-iodopyridine-2-carboxylic acid, methyl ester (1.1 g, 3.0 mmol), 4-bromo-2-fluoro-3-methoxyphenyl boronic acid (1.3 g, 4.5 mmol) and cesium fluoride (0.60 g, 4.0 mmole) in dimethoxyethane (2 mL) and water (2 mL) was de-aerated with a stream of nitrogen for 15 minutes before adding dichlorobis(triphenylphosphine) palladium (0.25 g, 0.4 mmol) and then heated to 85° C. for 2 hours. The reaction mixture was diluted with water (15 mL) and extracted with ethyl acetate (2×15 mL). The combined extracts were washed with brine, dried (sodium sulfate) and concentrated. The residue was purified by chromatography (33% ethyl acetate in hexanes) to give 4-acetylamino-6-(4-bromo-2-fluoro-3-methoxyphenyl)-3-chloropyridine-2-carboxylic acid, methyl ester (1.2 g, 2.8 mmol): mp 164-165° C.

The following compounds were prepared according the procedure in Example 52.

4-Acetylamino-3-chloro-6-(2,4,6-trifluoro-3-methyoxyphenyl)pyridine-2-carboxylic acid, methyl ester (used without further purification).

4-Acetylamino-3-chloro-(2,4-difluoro-3-methoxyphenyl) pyridine-2-carboxylic acid, methyl ester (Compound 28): mp 114-115° C.

4-Acetylamino-3-chloro-(2-chloro-4-fluoro-3-methoxyphenyl)pyridine-2-carboxylic acid, methyl ester (Compound 29): mp 153-154.5° C.

53. Preparation of 4-acetylamino-3-chloro-6-[2,4-dichloro-3-(1-fluoroethyl)phenyl]pyridine-2-carboxylic acid methyl ester A solution of 2,4 dichloro-3-(1-fluoroethyl)-bromobenzene (3.4 g, 12.5 mmol), 4-acetylamino-3-chloro-6-trimethylstannnyl-pyridine-2-carboxylic acid, methyl ester (4.7 g, 12.5 mmol), copper iodide (0.4 g, 2.1 mmol), cesium fluoride (3.6 g, 25 mmol) and dichlorobis(triphenylphosphine)palladium (0.14 g, 2 mmol) in DMF (50 mL) was heated to 70° C. for 2 hours. Water (100 mL) was added the mixture extracted with ethyl acetate (2×100 mL). The combined extracts were washed with brine, dried (sodium sulfate) and concentrated. The residue was purified by chromatography (15%-30% ethyl acetate in hexanes) to give 4-acetylamino-3-chloro-6-[2,4 dichloro-3-(1-fluoroethyl)phenyl]pyridine-2-carboxylic acid, methyl ester which was used without further purification.

The following compounds were made according to the procedure of Example 53.

4-Acetylamino-3-chloro-(2,6-difluoro-3-methoxy-4-methylphenyl)pyridine-2-carboxylic acid, methyl ester: mp 134-136° C.

4-Acetylamino-3-chloro-6-(4-cyano-2,6-difluoro-3-methoxyphenyl)pyridine-2-carboxylic acid, methyl ester: mp 146-147° C.

4-Acetylamino-3-chloro-6-(4-chloro-3-dimethylamino-2,6-difluorophenyl)-pyridine-2-carboxylic acid, methyl ester (used without further purification).

4-Acetylamino-3-chloro-6-(4-chloro-2,6-difluoro-3-methoxyphenyl)pyridine-2-carboxylic acid, methyl ester (used without further purification).

4-Acetylamino-3-chloro-6-(2,4-dichloro-6-fluoro-3-methoxyphenyl)pyridine-2-carboxylic acid, methyl ester (used without further purification).

4-Acetylamino-3-chloro-6-(4-chloro-2,6-difluoro-3-ethoxyphenyl)pyridine-2-carboxylic acid, methyl ester: (used without further purification).

4-Acetylamino-3-chloro-6-[4-chloro-2-fluoro-3-(1-fluoroethyl)phenyl]pyridine-2-carboxylic acid, methyl ester (used without further purification).

4-Acetylamino-3-chloro-6-[2,4-dichloro-3-(difluoromethyl) phenyl]pyridine-2-carboxylic acid, methyl ester (Compound 30): mp 152-153° C.

4-Acetylamino-3-chloro-6-(4-chloro-3-ethyl-2-fluorophenyl)pyridine-2-carboxylic acid, methyl ester: GC/PCI (m/z=236).

4-Acetylamino-3-chloro-6-[4-chloro-2-fluoro-3-(1,2,2,2-tetrafluoroethyl)-phenyl)pyridine-2-carboxylic acid, methyl ester (Compound 31): LC/MS ESI (m/z=456).

4-Acetylamino-3-chloro-6-[4-chloro-2-fluoro-3-(1-fluoropropyl)-phenyl]pyridine-2-carboxylic acid, methyl ester (Compound 32): LC/MS ESI (m/z=416).

4-Acetylamino-3-chloro-6-(2,3,4-trifluorophenyl)pyridine-2-carboxylic acid, methyl ester (Compound 33): mp 169-171° C.

4-Acetylamino-3-chloro-6-(4-chloro-2-fluoro-3-methoxymethoxyphenyl)pyridine-2-carboxylic acid, methyl ester (Compound 34) mp 122-123° C.

4-Acetylamino-3-chloro-6-(4-chloro-2-fluoro-3-difluoromethoxyphenyl)pyridine, carboxylic acid, methyl ester (Compound 35): mp 146° C.

4-Acetylamino-3-chloro-6-(4-difluoromethyl-2-fluoro-3-methoxyphenyl)pyridine-2-carboxylic acid, methyl ester (used without purification).

4-Acetylamino-3-chloro-6-(2-fluoro-4-fluoromethyl-3-methoxyphenyl)pyridine-2-carboxylic acid, methyl ester (used without purification).

4-Acetylamino-3-chloro-6-(4-chloro-2,6-difluoro-3-methylphenyl)pyridine-2-carboxylic acid, methyl ester (used without purification).

4-Acetylamino-6-(2-bromo-4-chloro-3-methoxyphenyl)-3-chloropyridine-2-carboxylic acid, methyl ester (used without purification).

4-Acetylamino-6-(4-bromo-2,6-difluoro-3-methoxyphenyl)-3-chloropyridine-2-carboxylic acid, methyl ester (used without purification).

4-Acetylamino-3-chloro-6-(3-difluoromethyl-2,4,6-trifluorophenyl)pyridine-2-carboxylic acid, methyl ester (used without purification).

4-Acetylamino-3-chloro-6-(2-chloro-4-difluoromethyl-3-methoxyphenyl)pyridine-2-carboxylic acid, methyl ester (used without purification).

4-Acetylamino-3-chloro-6-(4-chloro-2,6-difluoro-3-difluoromethylphenyl)pyridine-2-carboxylic acid, methyl ester (used without purification).

4-Acetylamino-3-chloro-6-(2-chloro-4,6-difluoro-3-methoxyphenyl)pyridine-2-carboxylic acid, methyl ester (used without purification).

4-Acetylamino-3-chloro-6-(2,4-difluoro-3-ethoxyphenyl)pyridine-2-carboxylic acid, methyl ester (used without purification).

4-Acetylamino-3-chloro-6-(4-chloro-3-cyclopropyl-2-fluorophenyl)pyridine-2-carboxylic acid, methyl ester (used without purification).

4-Acetylamino-3-chloro-6-[4-chloro-2-fluoro-3-(2,2,2-trifluoroacetyl)phenyl]-pyridine-2-carboxylic acid, methyl ester (used without purification).

54. Preparation of 4-amino-3-chloro-6-(2-fluoro-3-methoxy-4-methylphenyl)pyridine-2-carboxylic acid, methyl ester (Compound 36)

A solution of 4-amino-3,6-dichloropyridine-2-carboxylic acid, methyl ester (0.24 g, 1.1 mmol), 2-fluoro-3-methoxy-4-methylphenyl boronic acid (0.30 g, 1.63 mmol) and cesium fluoride (3.0 g, 3.26 mmole) in dimethoxyethane (2 mL) and water (2 mL) was purged with a stream of nitrogen for 15 minutes before adding dichlorobis(triphenylphosphine) palladium (0.07 g, 0.1 mmol) and then heated to 85° C. for 2 hours. The reaction mixture was diluted with water (15 mL) and extracted with ethyl acetate (2×15 mL). The combined extracts were washed with brine, dried (sodium sulfate) and concentrated. The residue was purified by chromatography (33% ethyl acetate in hexanes) to give 4-amino-3-chloro-6-(2-fluoro-3-methoxy-4-methylphenyl)pyridine-2-carboxylic acid, methyl ester (0.08 g, 0.2 mmol): mp 95-96° C.

The following compounds were prepared according the procedure in Example 52.

4-Amino-3-chloro-6-[2,4-dichloro-3-(dimethylamino)phenyl]pyridine-2-carboxylic acid, methyl ester (Compound 37): $^1$H NMR (300 MHz, CDCl$_3$): δ 7.30 (d, 1H,), 7.19 (d, 1H,), 6.93 (s, 1H) 4.88 (bs, 2H), 3.96 (s, 3H), 2.88 (s, 6H).

4-Amino-3-chloro-6-[4-chloro-2-fluoro-3-(methylamino)phenyl]pyridine-2-carboxylic acid, methyl ester (Compound 38): mp 148-149° C.

4-Amino-3-chloro-6-[4-chloro-2-fluoro-3-(methoxycarbonyl)phenyl]pyridine-2-carboxylic acid, methyl ester (Compound 39): $^1$H NMR (300 MHz, CDCl$_3$): δ 7.53 (d, 1H,). 7.37 (d, 1H,), 6.94 (s, 1H), 4.97 (bs, 2H), 3.97 (s, 3H), 3.96 (s, 3H).

4-Acetylamino-3-chloro-6-(4-cyano-2,6-difluoro-3-methoxyphenyl)pyridine-2-carboxylic acid, methyl ester: mp 146-147° C.

4-Acetylamino-3-chloro-6-[4-chloro-3-(dimethylamino)-2,6-difluorophenyl]pyridine-2-carboxylic acid, methyl ester: $^1$H NMR (300 MHz, CDCl$_3$): δ 8.70 (s, 1H), 8.03 (bs, 1H), 7.03 (dd, 1H), 4.00 (s, 3H), 2.83 (d, 6H,), 2.32 (s, 3H).

4-Acetylamino-3-chloro-6-(2,6-difluoro-3-methoxy-4-methylphenyl)pyridine-2-carboxylic acid, methyl ester: mp 134-136° C.

4-Acetylamino-6-(4-bromo-2-chloro-3-methoxyphenyl)-3-chloropyridine-2-carboxylic acid, methyl ester: mp 129-130° C.

4-Acetylamino-3-chloro-6-(4-chloro-2,6-difluoro-3-methoxyphenyl)pyridine-2-carboxylic acid, methyl ester (Compound 40): mp 144-144.5° C.

55. Preparation of 4-amino-3-chloro-6-(4-chloro-2-fluoro-3-ethoxyphenyl)-pyridine-2-carboxylic acid methyl ester (Compound 41)

To a solution of 4-acetylamino-3-chloro-6-(4-chloro-2-fluoro-3-ethoxyphenyl)pyridine-2-carboxylic acid methyl ester (0.5 g, 0.0013 mol) in methanol (10 mL) was added acetyl chloride (1 mL) and the solution heated under reflux for 1 hour. Water (2 mL) was added and resulting solid collected and dried to give 4-amino-3-chloro-6-(4-chloro-2-fluoro-3-ethoxyphenyl)pyridine-2-carboxylic acid methyl ester: mp 154-156° C.

The following compounds were prepared according to the procedure of Example 55.

4-Amino-3-chloro-6-(4-chloro-2-fluoro-3-methoxyphenyl)pyridine-2-carboxylic acid methyl ester (Compound 42): mp 141-142° C.

4-Amino-3-chloro-6-(4-chloro-2-fluoro-5-methoxyphenyl)pyridine-2-carboxylic acid methyl ester (Compound 43): $^1$NMR (CDCl$_3$): δ 7.60 (d, 1H), 7.25 (s, 1H), 7.20 (m, 1H), 4.95 (bs, 2H), 4.05 (s, 3H), 3.95 (s, 3H).

4-Amino-3-chloro-6-(2,4-dichloro-3-methoxyphenyl)pyridine-2-carboxylic acid methyl ester (Compound 44): mp 168-170° C.

4-Amino-3-chloro-6-(2-fluoro-3-methoxy-4-trifluoromethylphenyl)pyridine-2-carboxylic acid methyl ester (Compound 45): mp 144-146° C.

4-Amino-3-chloro-6-(2-fluoro-3,4 methylenedioxyphenyl)pyridine-2-carboxylic acid methyl ester (Compound 46): mp 139-141° C.

4-Amino-3-chloro-6-(2,4-difluoro-3-methylphenyl)pyridine-2-carboxylic acid methyl ester (Compound 47): mp 129-130° C.

4-Amino-3-chloro-6-(2,4-dichloro-3-methylphenyl)pyridine-2-carboxylic acid methyl ester (Compound 48): $^1$NMR (CDCl$_3$): 7.30 (d, 1H), 7.25 (d, 1H), 6.95 (s, 1H).

4-Amino-3-chloro-6-(4-chloro-2-fluoro-3-methylphenyl)pyridine-2-carboxylic acid methyl ester (Compound 49): mp 116-118° C.

4-Amino-3-chloro-6-[4-chloro-3-(dimethylamino)-2,6-difluorophenyl]pyridine-2-carboxylic acid, methyl ester (Compound 50): $^1$H NMR (300 MHz, CDCl$_3$): δ 7.00 (dd, 1H,), 6.81 (s, 1H) 4.93 (bs, 2H), 3.96 (s, 3H), 2.81 (d, 6H,).

4-Amino-3-chloro-6-(2,6-difluoro-3-methoxy-4-methylphenyl)pyridine-2-carboxylic acid, methyl ester (Compound 51): Off white foam, $^1$H NMR (300 MHz, CDCl$_3$): δ 6.83 (s, 1H), 6.74 (dd, 1H,), 4.88 (bs, 2H), 3.97 (s, 3H), 3.84 (d, 3H,), 2.28 (s, 3H).

4-Amino-6-(4-bromo-2-chloro-3-methoxyphenyl)-3-chloropyridine-2-carboxylic acid, methyl ester (Compound 52): mp 154-155° C.

4-Amino-3-chloro-(2-chloro-4-difluoromethyl-6-fluoro-3-methoxyphenyl)pyridine-2-carboxylic acid, methyl ester (Compound 53): LC/MS (m/z=380).

4-Amino-3-chloro-6-(4-chloro-3-difluoromethyl-2,6-difluorophenyl)pyridine-2-carboxylic acid, methyl ester (Compound 54): LC/MS (m/z=383).

4-Amino-3-chloro-(2-chloro-4,6-difluoro-3-methoxyphenyl)pyridine-2-carboxylic acid, methyl ester (Compound 55): LC/MS (m/z=348).

4-Amino-3-chloro-6-(2,4,6-trifluoro-3-methyoxyphenyl)pyridine-2-carboxylic acid, methyl ester (Compound 56): HPLC-MS (m/z=346).

4-Amino-3-chloro-6-(2,4-dichloro-6-fluoro-3-methoxyphenyl)pyridine-2-carboxylic acid, methyl ester (Compound 57): HPLC-MS (m/z=378).

4-Amino-3-chloro-6-(4-chloro-2,6-difluoro-3-methoxyphenyl)pyridine-2-carboxylic acid, methyl ester (Compound 58): HPLC-MS (m/z=362).

4-Amino-3-chloro-6-(4-chloro-2,6-difluoro-3-ethoxyphenyl)pyridine-2-carboxylic acid, methyl ester (Compound 59): HPLC-MS (m/z=376).

4-Amino-3-chloro-6-(4-chloro-3-butoxy-2-fluorophenyl)pyridine-2-carboxylic acid, methyl ester (Compound 60): LC/MS ESI (m/z=386).

4-Amino-3-chloro-6-[4-chloro-2-fluoro-3-(1-fluoroethyl)phenyl]pyridine-2-carboxylic acid, methyl ester (Compound 61): LC/MS ESI (m/z=360).

4-Amino-3-chloro-6-(2,4-dichloro-3-difluoromethylphenyl)pyridine-2-carboxylic acid, methyl ester (Compound 62): LC/MS ESI (m/z=380).

4-Amino-3-chloro-6-[2,4-dichloro-3-(1-fluoro-1-ethylphenyl]pyridine-2-carboxylic acid, methyl ester (Compound 63): LC/MS ESI (m/z=362).

4-Amino-3-chloro-6-(4-chloro-3-ethyl-2-fluorophenyl)pyridine-2-carboxylic acid, methyl ester (Compound 64): mp 120-122° C.

4-Amino-3-chloro-6-[4-chloro-2-fluoro-3-(1,2,2,2-tetrafluoroethyl)phenyl]-pyridine-2-carboxylic acid, methyl ester (Compound 65): LC/MS ESI (m/z=414).

4-Amino-3-chloro-6-[4-chloro-2-fluoro-3-(1-fluoropropyl)phenyl]pyridine-2-carboxylic acid, methyl ester (Compound 66): $^1$H NMR (300 MHz, CDCl$_3$): δ 7.90 (m, 1H), 7.25 (m, 1H), 7.10 (s, 1H), 5.96 (dq, 1H), 4.90 (bs, 2H), 4.05 (s, 3H), 2.30 (m, 1H), 2.05 (m, 1H), 1.05 (t, 3H).

4-Amino-3-chloro-6-(2,3,4-trifluorophenyl)pyridine-2-carboxylic acid, methyl ester (Compound 67): mp 163-164° C.

4-Amino-3-chloro-6-(4-chloro-2-fluoro-3-methoxymethoxyphenyl)pyridine-2-carboxylic acid, methyl ester (Compound 68): mp 99° C.

4-Amino-3-chloro-6-(4-chloro-2-fluoro-3-difluoromethoxyphenyl)pyridine-2-carboxylic acid, methyl ester (Compound 69): mp 164° C.

4-Amino-3-chloro-6-(2,4-difluoro-3-methoxyphenyl)pyridine-2-carboxylic acid, methyl ester (Compound 70): LC/MS (m/z=328).

4-Amino-3-chloro-6-(4-difluoromethyl-2-fluoro-3-methoxyphenyl)pyridine-2-carboxylic acid, methyl ester (Compound 71): mp 145-147° C.

4-Amino-3-chloro-6-(2-fluoro-4-fluoromethyl-3-methoxyphenyl)pyridine-2-carboxylic acid, methyl ester (Compound 72): LC/MS (m/z=342).

4-Amino-3-chloro-6-(2,4-difluoro-5-methoxyphenyl)pyridine-2-carboxylic acid, methyl ester (Compound 73): mp 128-130° C.

4-Amino-3-chloro-6-(2-chloro-4-fluoro-3-methoxyphenyl)pyridine-2-carboxylic acid, methyl ester (Compound 74): mp 145-146° C.

4-Amino-3-chloro-6-(4-chloro-2,6-difluoro-3-methylphenyl)pyridine-2-carboxylic acid, methyl ester (Compound 75): LC/MS (m/z=346).

4-Amino-6-(2-bromo-4-chloro-3-methoxyphenyl)-3-chloropyridine-2-carboxylic acid, methyl ester (Compound 76): LC/MS (m/z=405).

4-Amino-6-(4-bromo-2,6-difluoro-3-methoxyphenyl)-3-chloropyridine-2-carboxylic acid, methyl ester (Compound 77): LC/MS (m/z=407).

4-Amino-3-chloro-6-(3-difluoromethyl-2,4,6-trifluorophenyl)pyridine-2-carboxylic acid, methyl ester (Compound 78): LC/MS (m/z=366).

4-Amino-3-chloro-6-(2-chloro-4-difluoromethyl-3-methoxyphenyl)pyridine-2-carboxylic acid, methyl ester (Compound 79): mp 134-136° C.

4-Amino-3-chloro-6-(2,4-difluoro-3-ethoxyphenyl)pyridine-2-carboxylic acid, methyl ester (Compound 80): mp 158-159° C.

4-Amino-3-chloro-6-(4-chloro-3-cyclopropyl-2-fluorophenyl)pyridine-2-carboxylic acid, methyl ester (Compound 81): mp 135-136.5° C.

4-Amino-3-chloro-6-[4-chloro-2-fluoro-3-(2,2,2-trifluoroacetyl)phenyl]pyridine-2-carboxylic acid, methyl ester (Compound 82): LC/MS (m/z=410).

56. Preparation of 4-amino-3-chloro-6-(4-chloro-2-fluoro-3-methanesulfinylphenyl)pyridine-2-carboxylic acid methyl ester (Compound 83) and 4-amino-3-chloro-6-(4-chloro-2-fluoro-3-methanesulfonylphenyl)pyridine-2-carboxylic acid methyl ester (Compound 84)

To a solution of 4-amino-3-chloro-6-(4-chloro-2-fluoro-3-methylthiophenyl)pyridine-2-carboxylic acid methyl ester (0.800 g, 2 mmol) in methylene chloride (20 mL) was slowly added peracetic acid (32% in acetic acid, 0.004 mol). The reaction mixture was quenched with sodium bisulfite (10% in water, 20 mL) and extracted with methylene chloride (20 mL). The organic phase was dried (sodium sulfate) and concentrated. The solid residue was purified by chromatography (15%-50% ethyl acetate in hexanes). The first fraction was 4-amino-3-chloro-6-(4-chloro-2-fluoro-3-methanesulfonylphenyl)pyridine-2-carboxylic acid methyl ester (0.250 g, 0.7 mmole): mp 108-110° C. The second fraction was 4-amino-3-chloro-6-(4-chloro-2-fluoro-3-methanesulfinylphenyl)pyridine-2-carboxylic acid methyl ester (0.100 g, 0.03 mmole): mp 122-124° C.

57. Preparation of 4-amino-3-chloro-6-(4-chloro-2-fluoro-3-fluoromethylthiophenyl)pyridine-2-carboxylic acid methyl ester (Compound 85)

To a solution of 4-amino-3-chloro-6-(4-chloro-2-fluoro-3-methylthiophenyl)pyridine-2-carboxylic acid, methyl ester (1.50 g, 4.1 mmol) in acetonitrile (40 mL) was added 1-chloromethyl-4-fluoro-1,4-diazoniabicyclo[2.2.2]octane-bis(tetrafluoroborate) (F-TEDA; SELECTFLUOR™ fluorinating agent; 1.48 g, 8.2 mmol) and the solution was stirred at ambient temperature for 2 hours. A saturated solution of sodium bicarbonate (25 mL) was added the solution extracted with methylene chloride (2×50 mL). The combined extracts were dried (sodium sulfate) and concentrated and the residue purified by chromatography (20%-50% ethyl acetate in hexanes) to give 4-amino-3-chloro-6-(4-chloro-2-fluoro-3-fluoromethylthiophenyl)pyridine-2-carboxylic acid methyl ester (0.09 g, 0.2 mmol): mp 104-105° C.

58. Preparation of 4-amino-3-chloro-6-(4-chloro-2-fluoro-3-methoxyphenyl)-pyridine-2-carboxylic acid, ethyl ester (Compound 86)

To a solution of 4-amino-3-chloro-6-(4-chloro-2-fluoro-3-methoxyphenyl)pyridine-2-carboxylic acid, methyl ester (200 mg, 0.9 mmol) in ethanol (5 mL) was added a catalytic amount of titanium tetraisopropoxide and the solution heated under reflux for 2 hours. The solution was cooled and partitioned between ethyl acetate (10 mL) and water (10 mL) and the organic phase was dried (sodium sulfate) and concentrated. The residue was passed over a plug of silica gel (1:1 ethyl acetate:hexanes) to give 4-amino-3-chloro-6-(4-chloro-2-fluoro-3-methoxyphenyl)pyridine-2-carboxylic acid, ethyl ester (150 mg. 0.6 mmol): mp 74-75° C.

The following compounds were prepared according to the procedure in Example 58.
4-Amino-3-chloro-6-(4-chloro-2-fluoro-3-methoxyphenyl) pyridine-2-carboxylic acid, 2-butoxy-ethyl ester (Compound 87): LC/MS (m/z=430).
4-Amino-3-chloro-6-(4-chloro-2,6-difluoro-3-methoxyphenyl)pyridine-2-carboxylic acid, butyl ester (Compound 88): LC/MS (m/z=404).
4-Amino-3-chloro-6-(2,4-dichloro-3-methoxyphenyl)pyridine-2-carboxylic acid, butyl ester (Compound 89): LC/MS ESI (m/z=402).
4-Amino-3-chloro-6-(4-bromo-2-fluoro-3-methoxyphenyl) pyridine-2-carboxylic acid, butyl ester (Compound 90): LC/MS ESI (m/z=430).
4-Amino-3-chloro-6-[4-chloro-2-fluoro-3-(1-fluoroethyl) phenyl)pyridine-2-carboxylic acid, butyl ester (Compound 91): LC/MS ESI (m/z=402).
4-Amino-3-chloro-6-(4-chloro-2-fluoro-3-methoxyphenyl) pyridine-2-carboxylic acid, 2-butoxy-ethyl ester (Compound 92): mp 72-74° C.

59. Preparation of 4-amino-3-chloro-6-(4-cyano-2,6-difluoro-3-methoxyphenyl)pyridine-2-carboxylic acid A slurry of 4-acetylamino-3-chloro-6-(4-cyano-2,6-difluoro-3-methoxyphenyl)pyridine (0.13 g, 0.33 mmol) in methanol (5 mL) was treated with 1N sodium hydroxide (1.7 mL) and stirred at ambient temperature for 1 hour. The solution was diluted with water (15 mL) and acidified with 1N hydrochloric acid (1.7 mL) and the solid collected (0.095 g).

Analysis by $^1$H NMR showed the 4-amino-3-chloro-6-(4-cyano-2,6-difluoro-3-methoxyphenyl)pyridine-2-carboxylic acid and an impurity. This material was used without further purification.

The following compounds were prepared according to the procedure of example 59.
4-Amino-3-chloro-6-(2,6-difluoro-3-methoxy-4-methylphenyl)pyridine-2-carboxylic acid (Compound 93): mp 167-168° C.
4-Amino-3-chloro-6-(4-chloro-2,6-difluoro-3-dimethylaminophenyl)pyridine-2-carboxylic acid (Compound 94): mp 171-172° C.

60. Preparation of 4-amino-3-chloro-6-(4-cyano-2,6-difluoro-3-methoxyphenyl)pyridine-2-carboxylic acid, methyl ester (Compound 95)

A slurry of 4-amino-3-chloro-6-(4-cyano-2,6-difluoro-3-methoxyphenyl)pyridine-2-carboxlic acid in tetrahydrofuran (10 mL) and methanol (3 mL) was treated with trimethylsilyldiazomethane (0.64 g, 0.28 mL of a 2M solution in hexanes) at ambient temperature. After 1 hour the reaction mixture was quenched with acetic acid (2 mL) and water (10 mL). The mixture was extracted with ethyl acetate (2×20 mL) and the combined extracts dried (Na$_2$SO$_4$), and concentrated. The residue was purified by chromatography (30-100% ethyl acetate in hexanes) to give 4-amino-3-chloro-6-(4-cyano-2, 6-difluoro-3-methoxyphenyl)pyridine-2-carboxylic acid, methyl ester (0.083 g, 0.24 mmol): $^1$H NMR (CDCl$_3$) δ 7.15 (dd, 1H), 6.85 (s, 1H), 4.98 (bs, 2H), 4.08 (d, 3h), 3.98 (s, 3H).

61. Preparation of 4-Amino-3-chloro-6-(4-chloro-2-fluoro-3-(2,2-difluoroethoxy)phenyl)pyridine-2-carboxylic acid (Compound 96)

A solution of 4-amino-3-chloro-6-(4-chloro-2-fluoro-3-(2,2-difluoroethoxy)phenyl)pyridine-2-carboxylic acid methyl ester (0.300 g, 0.0008 mol) in methanol (5 mL) and sodium hydroxide (1N, 2 mL) was heated to reflux 1 hour and then acidified to pH 3 (concentrated hydrochloric acid) and allowed to cool. The resulting solid was collected and dried to give 4-amino-3-chloro-6-(4-chloro-2-fluoro-3-(2,2-difluoroethoxy)phenyl)pyridine-2-carboxylic acid (0.270 g, 0.0007 mol): mp 183-184° C. dec.

The following compounds were prepared according to the procedure of Example 61.
4-Amino-3-chloro-(2,4-difluoro-3-methylphenyl)pyridine-2-carboxylic acid (Compound 97): mp 189-190° C. dec.
4-Amino-3-chloro-6-(2,4-dichloro-3-methylphenyl)pyridine-2-carboxylic acid (Compound 98): mp 170-172° C. dec.
4-Amino-3-chloro-6-(4-chloro-2-fluoro-3-methylphenyl) pyridine-2-carboxylic acid (Compound 99): mp 179-181° C. dec.
4-Amino-3-chloro-6-(4-chloro-2-fluoro-3-methoxyphenyl) pyridine-2-carboxylic acid (Compound 100): mp 174-175° C. dec.
4-Amino-3-chloro-6-(4-chloro-2-fluoro-5-methoxyphenyl) pyridine-2-carboxylic acid (Compound 101): $^1$NMR (DMSO-d$_6$): δ 13.80 (bs, 1H) 7.55 (m, 2H), 7.25 (s, 1H), 3.95 (s, 3H).
4-Amino-3-chloro-6-(4-chloro-2-fluoro-3-ethoxyphenyl) pyridine-2-carboxylic acid (Compound 102): mp 177-178° C. dec.

4-Amino-3-chloro-6-(2,4-dichloro-3-methoxyphenyl)pyridine-2-carboxylic acid (Compound 103): mp 179-180° C. dec.

4-Amino-3-chloro-6-(4-chloro-2-fluoro-3-methylthiophenyl)pyridine-2-carboxylic acid (Compound 104): $^1$NMR (DMSO-d$_6$) δ 13.80 (bs, 1H), 7.90 (t, 1H), 7.55 (d, 1H), 7.10 (s, 1H), 6.95 (bs, 2H), 2.50 (s, 3H).

4-Amino-3-chloro-6-(4-chloro-2-fluoro-3-methoxymethylphenyl)pyridine-2-carboxylic acid (Compound 105): mp 187-188° C. dec.

4-Amino-3-chloro-6-(4-chloro-2-fluoro-3-difluoromethylphenyl)pyridine-2-carboxylic acid (Compound 106): mp 182-183° C. dec.

4-Amino-3-chloro-6-(2-fluoro-3-methoxy-4-trifluoromethylphenyl)pyridine-2-carboxylic acid (Compound 107): mp 177-178° C. dec.

4-Amino-3-chloro-6-(2-fluoro-3,4-methylenedioxyphenyl)pyridine-2-carboxylic acid (Compound 108): mp 202-203° C. dec.

4-Amino-3-chloro-6-(4-chloro-2-fluoro-5-ethoxyphenyl)pyridine-2-carboxylic acid (Compound 109): mp 178-179° C. dec.

4-Amino-3-chloro-6-(2,4-dichloro-3-methoxyphenyl)pyridine-2-carboxylic acid (Compound 110): mp 187-188° C. dec.

4-Amino-3-chloro-6-(4-chloro-5-dimethyamino-2-fluorophenyl)pyridine-2-carboxylic acid (Compound III): mp 180-181° C. dec.

4-Amino-3-chloro-6-(4-chloro-3-dimethyamino-2-fluorophenyl)pyridine-2-carboxylic acid (Compound 112): mp 185-186° C. dec.

4-Amino-3-chloro-6-(4-chloro-2-fluoro-3-methoxyethoxyphenyl)pyridine-2-carboxylic acid (Compound 113): mp 169-170° C. dec.

4-Amino-3-chloro-6-(4-chloro-2-fluoro-3-fluoromethylphenyl)pyridine-2-carboxylic acid (Compound 114): $^1$H NMR (DMSO-d$_6$): 8.00 (dt, 1H) 7.50 (dd, 1H), 6.90 (bs, 2H), 5.60 (dd, 1H).

4-Amino-3-chloro-5-fluoro-6-(2-fluoro-3,4-methylenedioxyphenyl)pyridine-2-carboxylic acid (Compound 115): mp 179-180° C.

4-Amino-3-chloro-6-[4-chloro-3-(diethylamino)-2-fluorophenyl]pyridine-2-carboxylic acid (Compound 116): mp 174-175° C.

4-Amino-3-chloro-6-[2,4-dichloro-3-(dimethylamino)phenyl]pyridine-2-carboxylic acid (Compound 117): mp 177-178° C.

4-Amino-3-chloro-6-[4-chloro-2-fluoro-3-(methylamino)phenyl]pyridine-2-carboxylic acid (Compound 118): mp 185-186° C.

4-Amino-3-chloro-6-(2-fluoro-3-methoxy-4-methylphenyl)pyridine-2-carboxylic acid (Compound 119): mp 178-179° C.

4-Amino-6-(4-bromo-2-fluoro-3-methoxyphenyl)-3-chloropyridine-2-carboxylic acid (Compound 120): mp 176-177° C.

4-Amino-6-(4-bromo-2-chloro-3-methoxyphenyl)-3-chloropyridine-2-carboxylic acid (Compound 121): mp 192-193° C.

4-Amino-3-chloro-6-(4-chloro-2-fluoro-5-methoxyphenyl)-5-fluoropyridine-2-carboxylic acid (Compound 122): mp 180-181° C.

4-Amino-3-chloro-6-(4-chloro-2-fluoro-3-methoxyphenyl)-5-fluoropyridine-2-carboxylic acid (Compound 123): mp 178-179° C.

4-Amino-3-chloro-6-(4-chloro-3-butoxy-2-fluorophenyl)pyridine-2-carboxylic acid (Compound 124): mp 157-158° C. dec.

4-Amino-6-[2,4 dichloro-3-(1-fluoroethyl)phenyl]pyridine-2-carboxylic acid (Compound 125): mp 169-170° C. dec.

4-Amino-3-chloro-6-(2,4-dichloro-3-difluoromethylphenyl)pyridine-2-carboxylic acid (Compound 126): mp 182-183° C. dec.

4-Amino-3-chloro-6-[2,4-dichloro-3-(1-fluoro-1-methylethylphenyl)pyridine-3-carboxylic acid (Compound 127): mp>250° C.

4-Amino-3-chloro-6-(4-chloro-3-ethyl-2-fluorophenyl)pyridine-2-carboxylic acid (Compound 128): mp 192-193° C. dec.

4-Amino-3-chloro-6-[4-chloro-2-fluoro-3-(1,2,2,2-tetrafluoroethyl)-phenyl]pyridine-2-carboxylic acid (Compound 129): mp 175-176° C. dec.

4-Amino-3-chloro-6-[4-chloro-2-fluoro-3-(1-fluoropropyl)phenyl]pyridine-2-carboxylic acid, methyl ester (Compound 130): mp 165-167° C. dec.

4-Amino-3-chloro-6-(2,3,4-trifluorophenyl)pyridine-2-carboxlic acid (Compound 131): mp. 178-179° C. dec.

4-Amino-3-chloro-6-(4-chloro-2-fluoro-3-methoxymethoxyphenyl)pyridine-2-carboxylic acid (Compound 132): mp. 159° C. dec.

4-Amino-3-chloro-6-(4-chloro-2,6-difluoro-3-methoxyphenyl)pyridine-2-carboxylic acid (Compound 133): LC/MS (m/z=293).

4-Amino-3-chloro-6-(4-chloro-3-difluoromethoxy-2-fluorophenyl)pyridine-2-carboxylic acid (Compound 134): mp 179° C. dec.

62. Preparation of 4-amino-3-chloro-6-(4-chloro-2-fluoro-3-methoxyphenyl)-pyridine-2-carboxylic acid, triethyl amine salt (Compound 135)

To solution of 4-amino-3-chloro-6-(4-chloro-2-fluoro-3-methoxyphenyl)-pyridine-2-carboxylic acid (1.0 g, 3.1 mmol) in methanol (30 mL) was added triethylamine (10 mL) and the solution stirred at ambient temperature for 1 hour and was then concentrated to give 4-amino-3-chloro-6-(4-chloro-2-fluoro-3-methoxyphenyl)pyridine-2-carboxylic acid, triethylamine salt (1.1 g, 2.6 mmol): $^1$NMR (DMSO-d$_6$): δ 7.60 (m, 1H), 7.45 (m, 1H), 7.00 (s, 1H), 4.00 (s, 3H), 3.00 (t, 6H), 1.15 (q, 9H).

The following compound was prepared according to the procedure of Example 62.

4-Amino-3-chloro-6-(2,4 dichloro-3-methoxyphenyl)pyridine-2-carboxylic acid, triethyl amine salt (Compound 136): $^1$NMR (DMSO-d$_6$) δ 7.55 (d, 1H), 7.435 (d, 1H), 7.00 (s, 1H), 4.00 (s, 3H), 3.00 (t, 6H), 1.15 (q, 9H).

63. Preparation of Herbicidal Compositions

In the following illustrative compositions, parts and percentages are by weight.

Emulsifiable Concentrates

| Formulation A | |
|---|---|
| | WT % |
| Compound 1 | 26.2 |
| Polyglycol 26-3 | 5.2 |

-continued

Formulation A

| | WT % |
|---|---|
| Nonionic emulsifier-(di-sec-butyl)-phenyl-poly(oxypropylene)block polymer with (oxyethylene). The polyoxyethelene content is about 12 moles. | |
| Witconate P12-20 (Anionic emulsifier-calcium dodecylbenzene sulfonate-60 wt. % active) | 5.2 |
| Aromatic 100 (Xylene range aromatic solvent) | 63.4 |

Formulation B

| | WT % |
|---|---|
| Compound 12 | 3.5 |
| Sunspray 11N (paraffin oil) | 40.0 |
| Polyglycol 26-3 | 19.0 |
| Oleic acid | 1.0 |
| Xylene range aromatic solvent | 36.5 |

Formulation C

| | WT % |
|---|---|
| Compound 14 | 13.2 |
| Stepon C-65 | 25.7 |
| Ethomeen T/25 | 7.7 |
| Ethomeen T/15 | 18.0 |
| Xylene range aromatic solvent | 35.4 |

Formulation D

| | WT % |
|---|---|
| Compound 18 | 30.0 |
| Agrimer A1-10LC (emulsifier) | 3.0 |
| N-methyl-2-pyrrolidone | 67.0 |

Formulation E

| | WT % |
|---|---|
| Compound 41 | 10.0 |
| Agrimul 70-A (dispersant) | 2.0 |
| Amsul DMAP 60 (thickener) | 2.0 |
| Emulsogen M (emulsifier) | 8.0 |
| Attagel 50 (suspension aid) | 2.0 |
| Crop oil | 76.0 |

These concentrates can be diluted with water to give emulsions of suitable concentrations for controlling weeds.

Wettable Powders

Formulation F

| | WT % |
|---|---|
| Compound 95 | 26.0 |
| Polyglycol 26-3 | 2.0 |
| Polyfon H | 4.0 |
| Zeosyl 100 (Precipitated hydrated $SiO_2$) | 17.0 |
| Barden clay + inerts | 51.0 |

Formulation G

| | WT % |
|---|---|
| Compound 101 | 62.4 |
| Polyfon H (sodium salt of lignin sulfonate) | 6.0 |
| Sellogen HR (sodium naphthalene sulfonate) | 4.0 |
| Zeosyl 100 | 27.6 |

Formulation H

| | WT % |
|---|---|
| Compound 109 | 1.4 |
| Kunigel V1 (carrier) | 30.0 |
| Stepanol ME Dry (wetter) | 2.0 |
| Tosnanon GR 31A (binder) | 2.0 |
| Kaolin NK-300 Clay (filler) | 64.6 |

The active ingredient is applied to the corresponding carriers and then these are mixed and ground to yield wettable powders of excellent wettability and suspension power. By diluting these wettable powders with water it is possible to obtain suspensions of suitable concentrations for controlling weeds.

Water Dispersible Granules

Formulation I

| | WT % |
|---|---|
| Compound 63 | 26.0 |
| Sellogen HR | 4.0 |
| Polyfon H | 5.0 |
| Zeosyl 100 | 17.0 |
| Kaolinite clay | 48.0 |

The active ingredient is added to the hydrated silica, which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling weeds.

Granules

Formulation J

| | WT % |
|---|---|
| Compound 114 | 5.0 |
| Celetom MP-88 | 95.0 |

The active ingredient is applied in a polar solvent such as N-methyl pyrollidinone, cyclohexanone, gamma-butyrolactone, etc. to the Celetom MP 88 carrier or to other suitable carriers. The resulting granules can be applied by hand, granule applicator, airplane, etc. in order to control weeds.

Formulation K

| | WT % |
|---|---|
| Compound 117 | 1.0 |
| Polyfon H | 8.0 |
| Nekal BA 77 | 2.0 |
| Zinc Stearate | 2.0 |
| Barden Clay | 87.0 |

All materials are blended and ground to a powder then water is added and the clay mixture is stirred until a paste is formed. The mixture is extruded through a die to provide granules of proper size.

Water Soluble Liquids

Formulation L

| | WT % |
|---|---|
| Compound 136 | 3.67 |
| Monoethanolamine pH buffer | 0.5 |
| Water | 95.83 |

The active ingredient is dissolved in an appropriate amount of water and the additional monoethanolamine is added as a buffer. A water-soluble surfactant may be added. Other aids may be incorporated to improve physical, chemical and/or formulation properties.

64. Evaluation of Postemergence Herbicidal Activity

Seeds or nutlets of the desired test plant species were planted in Sun Gro MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 days in a greenhouse with an approximate 15 hour photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 mL glass vial and was dissolved in 4 mL of a 97:3 v/v (volume/volume) mixture of acetone and dimethyl sulfoxide (DMSO) to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 (v/v) mixture of acetone and dimethyl sulfoxide (DMSO) and 10 mL of an aqueous mixture containing acetone, water, isopropyl alcohol, DMSO, Atplus 411F crop oil concentrate, and Triton X-155 surfactant in a 48.5:39:10:1.5:1.0:0.02 (v/v) ratio to obtain 1/2×, 1/4×, 1/8× and 1/16× rates of the high rate. Compound requirements are based upon a 12 mL application volume at a rate of 187 L/ha. Formulated compounds were applied to the plant material with an overhead Mandel track sprayer equipped with a 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. After 14 days, the condition of the test plants as compared with that of the untreated plants was determined visually and scored on a scale of 0 to 100 percent 0 corresponds to no injury and 100 corresponds to complete kill.

By applying the well-accepted probit analysis as described by J. Berkson in *Journal of the American Statistical Society*, 48, 565 (1953) and by D. Finney in "*Probit Analysis*" Cambridge University Press (1952), the above data can be used to calculate $GR_{50}$ and $GR_{80}$ values, which are defined as growth reduction factors that correspond to the effective dose of herbicide required to kill or central 50 percent or 80 percent, respectively, of a target plant.

Some of the compounds tested, application rates employed, plant species tested, and results are given in Table 1.

TABLE 1

Post-emergent control of weeds.

| | Rate | % Control | | |
|---|---|---|---|---|
| Compound # | (g ai/ha) | ABUTH | AMARE | CHEAL |
| 1 | 140 | 85 | 100 | 100 |
| 2 | 140 | 85 | 90 | 80 |
| 3 | 140 | 100 | 100 | 80 |
| 4 | 140 | 100 | 100 | 85 |
| 5 | 140 | 100 | 35 | 90 |
| 6 | 140 | 90 | 100 | 95 |
| 7 | 140 | 100 | 90 | 95 |
| 8 | 140 | 80 | 100 | 95 |
| 9 | 140 | 85 | 100 | 100 |
| 10 | 140 | 90 | 100 | 100 |
| 11 | 140 | 90 | 95 | 80 |
| 12 | 140 | 100 | 100 | 100 |
| 13 | 140 | 100 | 100 | 90 |
| 14 | 140 | 100 | 100 | 100 |

TABLE 1-continued

Post-emergent control of weeds.

| Compound # | Rate (g ai/ha) | % Control ABUTH | AMARE | CHEAL |
|---|---|---|---|---|
| 15 | 140 | 100 | 100 | 100 |
| 16 | 140 | 100 | 100 | 100 |
| 17 | 140 | 100 | 100 | 100 |
| 25 | 140 | 100 | 100 | 100 |
| 26 | 140 | 100 | 100 | 100 |
| 27 | 140 | 100 | 90 | 100 |
| 28 | 140 | 100 | 100 | 95 |
| 29 | 140 | 95 | 40 | 98 |
| 30 | 140 | 100 | 90 | 95 |
| 32 | 140 | 60 | 80 | 50 |
| 33 | 140 | 95 | 95 | 90 |
| 36 | 140 | 100 | 100 | 100 |
| 37 | 140 | 100 | 100 | 100 |
| 38 | 140 | 100 | 100 | 100 |
| 39 | 140 | 90 | 75 | 95 |
| 40 | 140 | 95 | 95 | 100 |
| 41 | 140 | 95 | 85 | 98 |
| 42 | 140 | 100 | 100 | 100 |
| 43 | 140 | 100 | 100 | 100 |
| 44 | 140 | 100 | 100 | 100 |
| 45 | 140 | 100 | 80 | 95 |
| 46 | 140 | 100 | 100 | 95 |
| 47 | 140 | 100 | 100 | 100 |
| 48 | 101 | 98 | 80 | 85 |
| 49 | 140 | 100 | 80 | 90 |
| 50 | 140 | 100 | 100 | 100 |
| 51 | 140 | 100 | 100 | 100 |
| 52 | 140 | 100 | 100 | 95 |
| 53 | 140 | 70 | 80 | 95 |
| 54 | 140 | 100 | 100 | 100 |
| 55 | 140 | 100 | 100 | 90 |
| 56 | 140 | 100 | 100 | 100 |
| 57 | 140 | 100 | 100 | 100 |
| 58 | 140 | 100 | 100 | 100 |
| 59 | 140 | 100 | 90 | 90 |
| 60 | 140 | 55 | 90 | 90 |
| 61 | 140 | 100 | 100 | 100 |
| 62 | 140 | 100 | 100 | 100 |
| 63 | 140 | 100 | 100 | 100 |
| 64 | 140 | 95 | 100 | 100 |
| 65 | 140 | 95 | 100 | 90 |
| 66 | 140 | 90 | 100 | 95 |
| 67 | 140 | 100 | 100 | 100 |
| 68 | 140 | 95 | 100 | 100 |
| 69 | 140 | 100 | 100 | 100 |
| 70 | 140 | 100 | 100 | 100 |
| 71 | 140 | 100 | 80 | 85 |
| 72 | 140 | 100 | 20 | 80 |
| 73 | 140 | 90 | 100 | 100 |
| 74 | 140 | 100 | 90 | 100 |
| 75 | 140 | 100 | 95 | 95 |
| 76 | 140 | 100 | 100 | 100 |
| 77 | 140 | 100 | 100 | 100 |
| 78 | 140 | 90 | 100 | 100 |
| 79 | 140 | 95 | 90 | 100 |
| 80 | 140 | 100 | 100 | 95 |
| 81 | 140 | 100 | 100 | 95 |
| 82 | 140 | 100 | 100 | 95 |
| 83 | 140 | 90 | 85 | 85 |
| 84 | 140 | 80 | 75 | 70 |
| 85 | 140 | 100 | 95 | 100 |
| 86 | 140 | 100 | 100 | 100 |
| 87 | 140 | 100 | 100 | 100 |
| 90 | 140 | 100 | 85 | 100 |
| 91 | 140 | 95 | 100 | 100 |
| 92 | 140 | 100 | 100 | 100 |
| 93 | 140 | 100 | 100 | 100 |
| 94 | 140 | 100 | 100 | 100 |
| 95 | 140 | 100 | 85 | 90 |
| 96 | 140 | 50 | 100 | 90 |
| 97 | 140 | 65 | 85 | 80 |
| 98 | 140 | 90 | 70 | 80 |
| 99 | 140 | 80 | 90 | 90 |
| 100 | 140 | 100 | 100 | 100 |
| 101 | 140 | 100 | 100 | 100 |
| 102 | 140 | 80 | 85 | 95 |
| 103 | 140 | 95 | 100 | 100 |
| 104 | 140 | 85 | 80 | 80 |
| 105 | 140 | 95 | 98 | 85 |
| 106 | 140 | 90 | 100 | 90 |
| 107 | 140 | 100 | 80 | 90 |
| 108 | 140 | 100 | 100 | 95 |
| 110 | 140 | 80 | 90 | 85 |
| 112 | 140 | 100 | 100 | 100 |
| 114 | 140 | 95 | 85 | 95 |
| 115 | 140 | 100 | 100 | 100 |
| 116 | 140 | 80 | 90 | 100 |
| 117 | 140 | 100 | 100 | 100 |
| 118 | 140 | 100 | 100 | 100 |
| 119 | 140 | 100 | 100 | 95 |
| 120 | 140 | 100 | 90 | 95 |
| 121 | 140 | 100 | 95 | 90 |
| 123 | 140 | 100 | 100 | 100 |
| 126 | 140 | 90 | 100 | 100 |
| 127 | 140 | 90 | 100 | 100 |
| 129 | 140 | 85 | 95 | 90 |
| 130 | 140 | 80 | 95 | 95 |
| 131 | 140 | 100 | 100 | 100 |
| 134 | 140 | 95 | 100 | 90 |

ABUTH = velvetleaf (*Abutilon theophrasti*)
AMARE = redroot pigweed (*Amaranthus retroflexus*)
CHEAL = lambsquarter (*Chenopodium album*)

65. Evaluation of Preemergence Herbicidal Activity

Seeds of the desired test plant species were planted in a soil matrix prepared by mixing a loam soil (43 percent silt, 19 percent clay, and 38 percent sand, with a pH of about 8.1 and an organic matter content of about 1.5 percent) and sand in a 70 to 30 ratio. The soil matrix was contained in plastic pots with a surface area of 113 square centimeters. When required to ensure good germination and healthy plants, a fungicide treatment and/or other chemical or physical treatment was applied.

A weighed amount, determined by the highest rate to be tested, of each test compound was placed in a 25 mL glass vial and was dissolved in 6 mL of a 97:3 v/v (volume/volume) mixture of acetone and DMSO to obtain concentrated stock solutions. If the test compound did not dissolve readily, the mixture was warmed and/or sonicated. The stock solutions obtained were diluted with 18 mL of a 0.1% v/v aqueous solution of Tween® 20 surfactant to obtain spray solutions containing the highest application rate. Additional application rates were obtained by serial dilution of 12 mL of the high rate solution into a solution containing 3 mL of 97:3 v/v (volume/volume) mixture of acetone and DMSO and 9 mL of the 0.1% v/v aqueous solution of Tween® 20 surfactant to obtain 1/2×, 1/4×, 1/8× and 1/16× rates of the high rate. Compound requirements are based upon a 12 mL application volume at a rate of 187 L/ha. Formulated compounds were applied to the plant material with an overhead Mandel track sprayer equipped with a 8002E nozzles calibrated to deliver 187 L/ha over an application area of 0.503 square meters at a spray height of 18 inches (43 cm) above the soil surface. Control plants were sprayed in the same manner with the solvent blank.

The treated pots and control pots were placed in a greenhouse maintained with an approximate 15 hour photoperiod and temperatures of about 23-29° C. during the day and 22-28° C. during the night. Nutrients and water were added on a regular basis and supplemental lighting was provided with overhead metal halide 1000-Watt lamp as necessary. The water was added by top-irrigation. After 20-22 days, the condition of the test plants that germinated and grew as compared with that of the untreated plants that emerged and grew was determined visually and scored on a scale of 0 to 100 percent where 0 corresponds to no injury and 100 corresponds to complete kill or no emergence.

Some of the compounds tested, application rates employed, plant species tested, and results are given in Table 2.

TABLE 2

Pre-emergent control of weeds.

| Compound # | Rate (g ai/ha) | % Control | | |
|---|---|---|---|---|
| | | ABUTH | AMARE | CHEAL |
| 1 | 140 | 80 | 100 | 90 |
| 3 | 140 | 98 | 100 | 95 |
| 10 | 280 | 40 | 50 | 80 |
| 12 | 140 | 100 | 100 | 100 |
| 14 | 140 | 100 | 100 | 100 |
| 15 | 140 | 60 | 100 | 100 |
| 16 | 140 | 90 | 100 | 100 |
| 26 | 140 | 10 | 10 | 90 |
| 27 | 140 | 100 | 100 | 90 |
| 41 | 140 | 80 | 50 | 90 |
| 42 | 140 | 100 | 100 | 100 |
| 43 | 140 | 98 | 100 | 100 |
| 44 | 140 | 95 | 30 | 95 |
| 49 | 140 | 100 | 100 | 99 |
| 50 | 140 | 100 | 100 | 100 |
| 52 | 140 | 100 | 100 | 90 |
| 58 | 140 | 100 | 100 | 100 |
| 59 | 140 | 90 | 100 | 60 |
| 62 | 140 | 100 | 100 | 100 |
| 63 | 140 | 100 | 100 | 100 |
| 64 | 140 | 80 | 100 | 100 |
| 70 | 140 | 100 | 100 | 100 |
| 74 | 140 | 100 | 95 | 95 |
| 77 | 140 | 100 | 100 | 100 |
| 82 | 140 | 90 | 100 | 100 |
| 93 | 140 | 100 | 100 | 100 |
| 94 | 140 | 100 | 100 | 100 |
| 95 | 140 | 90 | 90 | 90 |
| 96 | 140 | 20 | 70 | 40 |
| 99 | 140 | 100 | 100 | 95 |
| 100 | 140 | 100 | 100 | 100 |
| 101 | 140 | 100 | 100 | 100 |
| 102 | 140 | 85 | 95 | 0 |
| 103 | 123 | 90 | 100 | 100 |
| 104 | 140 | 100 | 100 | 80 |
| 105 | 140 | 100 | 100 | 95 |
| 108 | 140 | 90 | 100 | 90 |
| 110 | 140 | 100 | 40 | 40 |
| 111 | 140 | 35 | 100 | 100 |
| 112 | 140 | 100 | 100 | 100 |
| 113 | 140 | 0 | 0 | 55 |
| 115 | 140 | 100 | 100 | 100 |
| 116 | 140 | 100 | 100 | 75 |
| 121 | 140 | 100 | 100 | 100 |
| 122 | 140 | 100 | 100 | 100 |
| 123 | 140 | 100 | 100 | 100 |
| 125 | 140 | 100 | 100 | 100 |
| 131 | 140 | 90 | 100 | 100 |

ABUTH = velvetleaf (*Abutilon theophrasti*)
AMARE = redroot pigweed (*Amaranthus retroflexus*)
CHEAL = lambsquarter (*Chenopodium album*)

66. Evaluation of Herbicidal Activity in Transplanted Paddy Rice

Weed seeds or nutlets of the desired test plant species were planted in puddled soil (mud) prepared by mixing a non-sterilized mineral soil (28 percent silt, 18 percent clay, and 54 percent sand, with a pH of about 7.3 to 7.8 and an organic matter content of about 1.0 percent) and water at a ratio of 100 kg of soil to 19 L of water. The prepared mud was dispensed in 250 mL aliquots into 480 mL non-perforated plastic pots with a surface area of 91.6 square centimeters leaving a headspace of 3 centimeters in each pot. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 650 mL of mud contained in 960 mL non-perforated plastic pots with a surface area of 91.6 square centimeters 4 days prior to herbicide application. The paddy was created by filling the 3 centimeter headspace of the pots with water. When required to ensure good germination and healthy plants, a fungicide treatment and/or other chemical or physical treatment was applied. The plants were grown for 4-14 days in a greenhouse with an approximate 14 hour photoperiod which was maintained at about 29° C. during the day and 26° C. during the night. Nutrients were added as Osmocote (17:6:10, N:P:K+ minor nutrients) at 2 g per pot. Water was added on a regular basis to maintain the paddy flood, and supplemental lighting was provided with overhead metal halide 1000-Watt lamps as necessary. The plants were employed for testing when they reached the second or third true leaf stage.

A weighed amount, determined by the highest rate to be tested, of each test compound was placed in a 120 mL glass vial and was dissolved in 20 mL of acetone to obtain concentrated stock solutions. If the test compound did not dissolve readily, the mixture was warmed and/or sonicated. The concentrated stock solutions obtained were diluted with 20 mL of an aqueous mixture containing 0.01% Tween 20 (v/v). Application rates of 1/2×, 1/4×, 1/8× and 1/16× of the high rate were obtained by injecting an appropriate amount of the stock solution into the aqueous layer of the paddy. Control plants were treated in the same manner with the solvent blank.

The treated plants and control plants were placed in a greenhouse as described above and water was added as needed to maintain a paddy flood. After 3 weeks the condition of the test plants as compared with that of the control plants was determined visually and scored on a scale of 0 to 100 percent where 0 corresponds to no injury and 100 corresponds to complete kill.

Some of the compounds tested, application rates employed, plant species tested, and results are given in Table 3.

TABLE 3

Herbicidal Activity in Transplant Rice.

| Compound # | Rate (g ai/ha) | % Control | | | | |
|---|---|---|---|---|---|---|
| | | ORYSA | ECHCG | MOOVA | CYPDI | SCPJU |
| 4 | 17.5 | 0 | 0 | 100 | 95 | 70 |
| 5 | 70 | 0 | 20 | 100 | 100 | 90 |
| 7 | 70 | 10 | 100 | 100 | 100 | 85 |
| 17 | 35 | 0 | 70 | 100 | 100 | 90 |
| 27 | 17.5 | 0 | 45 | 100 | 100 | 99 |
| 38 | 70 | 0 | 50 | 100 | 100 | 95 |
| 41 | 17.5 | 10 | 50 | 100 | 100 | 90 |
| 42 | 17.5 | 5 | 40 | 100 | 100 | 90 |

TABLE 3-continued

Herbicidal Activity in Transplant Rice.

| Compound # | Rate (g ai/ha) | ORYSA | ECHCG | MOOVA | CYPDI | SCPJU |
|---|---|---|---|---|---|---|
| 44 | 70 | 0 | 50 | 90 | 100 | 95 |
| 46 | 35 | 0 | 20 | 100 | 100 | 100 |
| 52 | 70 | 0 | 60 | 99 | 100 | 95 |
| 58 | 17.5 | 0 | 30 | 100 | 100 | 50 |
| 61 | 35 | 0 | 80 | 100 | 100 | 100 |
| 70 | 70 | 0 | 45 | 100 | 95 | 95 |
| 77 | 35 | 0 | 70 | 100 | 100 | 99 |
| 86 | 70 | 10 | 25 | 100 | 100 | 95 |
| 88 | 70 | 10 | 100 | 100 | 100 | 100 |
| 89 | 70 | 0 | 85 | 100 | 100 | 90 |
| 90 | 17.5 | 0 | 30 | 100 | 100 | 90 |
| 91 | 35 | 0 | 99 | 100 | 100 | 99 |
| 92 | 17.5 | 0 | 40 | 100 | 99 | 90 |
| 100 | 17.5 | 10 | 30 | 100 | 100 | 80 |
| 103 | 70 | 10 | 40 | 100 | 100 | 95 |
| 120 | 35 | 0 | 40 | 100 | 100 | 95 |
| 125 | 70 | 5 | 100 | 100 | 100 | 100 |
| 135 | 17.5 | 10 | 30 | 100 | 100 | 85 |
| 136 | 35 | 0 | 15 | 100 | 100 | 80 |

ORYSA = rice (*Orysa sativa* var. *Japonica*)
ECHCG = *Echinochloa crus-galli*
SCPJU = *Scirpus juncoides*
CYPDI = *Cyperus difformis*
MOOVA = *Monochoria vaginalis*

67. Evaluation of Postemergence Herbicidal Activity in Cereal Crops

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters. When required to ensure good germination and healthy plants, a fungicide treatment and/or other chemical or physical treatment was applied. The plants were grown for 7-36 days in a greenhouse with an approximate 14 hour photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

A weighed amount, determined by the highest rate to be tested, of each test compound was placed in a 25 mL glass vial and was dissolved in 8 mL of a 97:3 v/v mixture of acetone and DMSO to obtain concentrated stock solutions. If the test compound did not dissolve readily, the mixture was warmed and/or sonicated. The concentrated stock solutions obtained were diluted with 16 mL of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio to obtain spray solutions containing the highest application rates. Additional application rates were obtained by serial dilution of 12 mL of the high rate solution into a solution containing 4 mL of 97:3 v/v mixture of acetone and DMSO and 8 mL of an aqueous mixture containing acetone, water, isopropyl alcohol, DMSO, Agri-dex crop oil concentrate, and Triton X-77 surfactant in a 48.5:39.0:10.0:1.5:1.0:0.02 v/v ratio to obtain 1/2×, 1/4×, 1/8× and 1/16× rates of the high rate. Compound requirements are based upon a 12 mL application volume at a rate of 187 L/ha. Formulated compounds were applied to the plant material with an overhead Mandel track sprayer equipped with a 8002E nozzles calibrated to deliver 187 L/ha over an application area of 0.503 square meters at a spray height of 18 inches (43 cm) above average plant canopy height. Control plants were sprayed in the same manner with the blank.

The treated plants and control plants were placed in a greenhouse as described above and watered by sub-irrigation to prevent wash-off of the test compounds. After 20-22 days, the condition of the test plants as compared with that of the control plants was determined visually and scored on a scale of 0 to 100 percent where 0 corresponds to no injury and 100 corresponds to complete kill.

Some of the compounds tested, application rates employed, plant species tested, and results are given in Table 4.

TABLE 4

Post-emergent Control of Several Key Weeds in Cereal Crops

| | | % Control | | | | | |
|---|---|---|---|---|---|---|---|
| Compound # | Rate (g ai/ha) | TRZAS | HORVS | GALAP | LAMPU | PAPRH | VERPE |
| 1 | 35 | 5 | 10 | 85 | 80 | 80 | 50 |
| 14 | 35 | 0 | 0 | 90 | 95 | 95 | 65 |
| 16 | 17.5 | 10 | 10 | 95 | 100 | 95 | 95 |
| 17 | 17.5 | 0 | 0 | 80 | 100 | 100 | 99 |
| 26 | 70 | 0 | 10 | 80 | 95 | 95 | 40 |
| 27 | 17.5 | 5 | 5 | 99 | 100 | 100 | 50 |
| 36 | 70 | 5 | 0 | 95 | 99 | 99 | 50 |
| 38 | 17.5 | 5 | 0 | 85 | 95 | 100 | 99 |
| 42 | 17.5 | 5 | 5 | 99 | 100 | 99 | 60 |
| 43 | 70 | 0 | 5 | 65 | 99 | 85 | 30 |
| 44 | 35 | 10 | 5 | 65 | 99 | 90 | 60 |
| 45 | 17.5 | 0 | 0 | 90 | 100 | 90 | 80 |
| 50 | 70 | 0 | 0 | 95 | 100 | 95 | 60 |

TABLE 4-continued

Post-emergent Control of Several Key Weeds in Cereal Crops

| Compound # | Rate (g ai/ha) | % Control | | | | | |
|---|---|---|---|---|---|---|---|
| | | TRZAS | HORVS | GALAP | LAMPU | PAPRH | VERPE |
| 51 | 35 | 0 | 0 | 95 | 70 | 100 | 30 |
| 56 | 70 | 0 | 10 | 100 | 99 | 100 | 95 |
| 58 | 17.5 | 0 | 0 | 100 | 100 | 99 | 60 |
| 61 | 17.5 | 10 | 0 | 85 | 99 | 90 | 75 |
| 65 | 35 | 15 | 5 | 85 | 95 | 90 | 40 |
| 70 | 17.5 | 0 | 0 | 99 | 100 | 99 | 60 |
| 71 | 17.5 | 0 | 0 | 95 | 95 | 95 | 50 |
| 73 | 70 | 0 | 0 | 95 | 99 | 95 | 60 |
| 77 | 17.5 | 0 | 0 | 99 | 100 | 99 | 65 |
| 87 | 17.5 | 0 | 0 | 100 | 100 | 100 | 50 |
| 90 | 17.5 | 0 | 10 | 99 | 100 | 95 | 25 |
| 91 | 17.5 | 20 | 10 | 90 | 100 | 60 | 45 |
| 92 | 17.5 | 0 | 0 | 99 | 100 | 95 | 30 |
| 100 | 17.5 | 10 | 5 | 90 | 100 | 95 | 65 |
| 101 | 70 | 10 | 5 | 60 | 99 | 100 | 60 |
| 103 | 35 | 0 | 0 | 60 | 95 | 100 | 75 |
| 120 | 17.5 | 0 | 0 | 80 | 95 | 95 | 50 |
| 133 | 17.5 | 0 | 0 | 100 | 99 | 100 | 70 |
| 135 | 17.5 | 0 | 0 | 90 | 100 | 100 | 60 |

TRZAS = wheat (*Triticum aestivum*)
HORVS = barley (*Hordeum vulare*)
GALAP = *Galium aparine*
LAMPU = *Lamium purpureum*
PAPRH = *Papaver rhoeas*
VERPE = *Veronica persica*

68. Evaluation of Postemergence Herbicidal Safening in Cereal Crops

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters. When required to ensure good germination and healthy plants, a fungicide treatment and/or other chemical or physical treatment was applied. The plants were grown for 7-36 days in a greenhouse with an approximate 14 hour photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of compound 42 and cloquintocet-mexyl alone and in combination. Weighed amounts were placed in 25 mL glass vials and dissolved in a volume of 97:3 v/v acetone/DMSO to obtain 9 mg ai/mL stock solutions. If the test compound did not dissolve readily, the mixture was warmed and/or sonicated. The concentrated stock solutions were diluted to 3 mg ai/mL with the addition of 2 volumes of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio. A dilution solution was prepared by mixing 1 volume of 97:3 v/v acetone/DMSO and 2 volumes of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio. Compound requirements are based upon a 12 mL application volume at a rate of 187 L/ha. Spray solutions of cloquintocet-mexyl and compound 42 mixtures were prepared by adding the stock solutions to the appropriate amount of dilution solution to form 12 mL spray solution with active ingredients at 1:1, 1:2, and 1:4 (herbicide:safener) ratios. Formulated compounds were applied to the plant material with an overhead Mandel track sprayer equipped with a 8002E nozzles calibrated to deliver 187 L/ha over an application area of 0.503 square meters at a spray height of 18 inches (43 cm) above average plant canopy height. Control plants were sprayed in the same manner with the solvent blank.

The treated plants and control plants were placed in a greenhouse as described above and watered by sub-irrigation to prevent wash-off of the test compounds. After 3 weeks the condition of the test plants as compared with that of the untreated plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Table 5.

TABLE 5

Safening of herbicidal injury on cereal crops

| Application Rate (g ai/ha) | | % Control | | | | | | | |
|---|---|---|---|---|---|---|---|---|---|
| | | TRZAS | | HORVW | | GALAP | | PAPRH | |
| #42 | Cloquintocetmexyl | Ob | Ex | Ob | Ex | Ob | Ex | Ob | Ex |
| 35 | 0 | 35 | — | 0 | — | 99 | — | 100 | — |
| 70 | 0 | 40 | — | 15 | — | 100 | — | 100 | — |
| 0 | 35 | 0 | — | 0 | — | 0 | — | 0 | — |
| 0 | 70 | 0 | — | 0 | — | 0 | — | 0 | — |
| 0 | 140 | 0 | — | 0 | — | 0 | — | 0 | — |
| 0 | 280 | 0 | — | 0 | — | 0 | — | 0 | — |
| 35 | 35 | 0 | 35 | 0 | 0 | 100 | 99 | 100 | 100 |
| 35 | 70 | 0 | 35 | 0 | 0 | 100 | 99 | 100 | 100 |
| 35 | 140 | 0 | 35 | 0 | 0 | 100 | 99 | 100 | 100 |
| 70 | 70 | 0 | 40 | 0 | 15 | 100 | 100 | 100 | 100 |
| 70 | 140 | 0 | 40 | 0 | 15 | 100 | 100 | 100 | 100 |
| 70 | 280 | 0 | 40 | 0 | 15 | 100 | 100 | 100 | 100 |

TRZAS = *Triticum aestivum* (spring wheat)
HORVW = *Hordeum vulgare* (winter barley)
GALAP = *Galium aparine*
PAPRH = *Papaver rhoeas*
Ob = observed values
Ex = expected, calculated values

69. Evaluation of Postemergence Herbicidal Activity of Mixtures in Cereal Crops Seeds of the desired test plant species were planted and reared as described in "Evaluation of Postemergence Herbicidal Safening in Cereal Crops" (section 37).

Treatments consisted of compound (as listed in Tables 6 and 7), fluroxypyr methylheptyl ester (MHE), and clopyralid monoethanolamine (MEA) salt alone and in combination. Weighed amounts were placed in 25 mL glass vials and dissolved in a volume of 97:3 v/v acetone/DMSO to obtain 4.5 mg ai/mL stock solutions. If the experimental compound did not dissolve readily, the mixture was warmed and/or sonicated. The concentrated stock solutions were diluted to 1.5 mg ai/mL with the addition of 2 volumes of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio. A dilution solution was prepared by mixing 1 volume of 97:3 v/v acetone/DMSO and 2 volumes of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio. Compound requirements are based upon a 12 mL application volume at a rate of 187 L/ha. Spray solutions of fluroxypyr MHE, clopyralid MEA, and experimental compound mixtures were prepared by adding the stock solutions to the appropriate amount of dilution solution to form 12 mL spray solution with active ingredients in two- and three-way combinations. Formulated compounds were applied to the plant material with an overhead Mandel track sprayer equipped with a 8002E nozzles calibrated to deliver 187 L/ha over an application area of 0.503 square meters at a spray height of 18 inches (43 cm) above average plant canopy. Control plants were sprayed in the same manner with the solvent blank.

The treated plants and control plants were placed in a greenhouse as described above and watered by sub-irrigation to prevent wash-off of the test compounds. After 3 weeks the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

The following equation was used to calculate the expected activity of mixtures containing three active ingredients, A, B, and C:

$$\text{Expected} = A + B + C - (A \times B + B \times C + A \times C)/100 + (A \times B \times C)/10000$$

A=observed efficacy of active ingredient A at the same concentration as used in the mixture.

B=observed efficacy of active ingredient B at the same concentration as used in the mixture.

C=observed efficacy of active ingredient C at the same concentration as used in the mixture.

Some of the compounds tested, application rates employed, plant species tested, and results are given in Table 6 and Table 7.

TABLE 6

Safening and synergistic activity of herbicidal combinations.

| Application Rate (g ai/ha) | | | | | % Control | | | | | |
|---|---|---|---|---|---|---|---|---|---|---|
| Compound #93 | Compound #74 | Compound #58 | Fluroxypyr MHE | Clopyralid MEA | TRZAS Ob | TRZAS Ex | HORVW Ob | HORVW Ex | MATCH Ob | MATCH Ex |
| 0 | 0 | 0 | 0 | 35 | 0 | — | 0 | — | 20 | — |
| 0 | 0 | 0 | 35 | 0 | 0 | — | 0 | — | 0 | — |
| 0 | 0 | 0 | 35 | 35 | 0 | 0 | 0 | 0 | 25 | 20 |
| 35 | — | — | 0 | 0 | 15 | — | 10 | — | 45 | — |
| 35 | — | — | 35 | 35 | 0 | 15 | 0 | 10 | 85 | 56 |
| — | 35 | — | 0 | 0 | 25 | — | 0 | — | 10 | — |
| — | 35 | — | 35 | 35 | 10 | 25 | 0 | 0 | 80 | 28 |
| — | — | 35 | 0 | 0 | 35 | — | 15 | — | 0 | — |
| — | — | 35 | 35 | 35 | 30 | 35 | 10 | 15 | 70 | 20 |

TRZAS = *Triticum aestivum* (spring wheat)
HORVW = *Hordeum vulgare* (winter barley)
MATCH = *Matricaria chamomilla*
MHE = methyl heptyl ester
MEA = monoethanolamine salt
Ob = observed values
Ex = expected, calculated values

TABLE 7

Safening and synergistic activity of herbicidal combinations.

| Application Rate (g ai/ha) | | | % Control | | | | | |
|---|---|---|---|---|---|---|---|---|
| Compound #42 | Clopyralid MEA | Fluroxypyr MHE | TRZAS Ob | TRZAS Ex | HORVW Ob | HORVW Ex | MATCH Ob | MATCH Ex |
| 35 | 0 | 0 | 30 | — | 25 | — | 50 | — |
| 70 | 0 | 0 | 45 | — | 30 | — | 60 | — |
| 0 | 35 | 0 | 0 | — | 0 | — | 5 | — |
| 0 | 70 | 0 | 0 | — | 0 | — | 40 | — |
| 0 | 0 | 35 | 0 | — | 0 | — | 0 | — |
| 0 | 0 | 70 | 0 | — | 0 | — | 0 | — |
| 0 | 35 | 35 | 0 | 0 | 0 | 0 | 20 | 5 |
| 0 | 70 | 70 | 0 | 0 | 0 | 0 | 20 | 40 |
| 35 | 35 | 0 | 25 | 30 | 15 | 30 | 99 | 52 |
| 70 | 70 | 0 | 40 | 45 | 25 | 30 | 100 | 76 |
| 35 | 0 | 35 | 30 | 30 | 15 | 25 | 50 | 50 |
| 70 | 0 | 70 | 35 | 45 | 20 | 30 | 90 | 60 |
| 35 | 35 | 35 | 30 | 30 | 15 | 25 | 70 | 52 |
| 70 | 70 | 70 | 30 | 45 | 25 | 30 | 99 | 76 |
| 35 | 70 | 35 | 20 | 30 | 15 | 25 | 99 | 70 |
| 35 | 35 | 70 | 10 | 30 | 15 | 25 | 99 | 52 |
| 70 | 35 | 35 | 30 | 45 | 25 | 30 | 70 | 62 |

TRZAS = *Triticum aestivum* (spring wheat)
HORVW = *Hordeum vulgare* (winter barley)
MATCH = *Matricaria chamomilla*
MHE = methyl heptyl ester
MEA = monoethanolamine salt
Ob = observed values
Ex = expected, calculated values

What is claimed is:

1. A compound of the formula

ArMetal wherein
Ar represents a polysubstituted aryl group selected from the group consisting of
a)

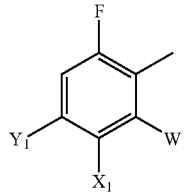

wherein
$W_1$ represents halogen;
$X_1$ represents F, Cl, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkyl, $C_1$-$C_4$ haloalkoxy, $C_1$-$C_4$ alkoxy-substituted $C_1$-$C_4$ alkyl, $C_1$-$C_4$ alkoxy-substituted $C_1$-$C_4$ alkoxy, —CN, —NR$_3$R$_4$ or fluorinated acetyl or propionyl;
$Y_1$ represents $C_1$-$C_4$ alkyl, $C_1$-$C_4$ haloalkyl, halogen or —CN, or, when $X_1$ and $Y_1$ are taken together, represents —O(CH$_2$)$_n$O— wherein n=1 or 2; and
$R_3$ and $R_4$ independently represent H or $C_1$-$C_4$ alkyl;
b)

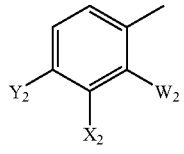

wherein
$W_2$ represents F or Cl;
$X_2$ represents F, Cl, —CN, —NO$_2$, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkyl, $C_1$-$C_4$ haloalkoxy, $C_1$-$C_4$ alkoxy-substituted $C_1$-$C_4$ alkyl, $C_1$-$C_4$ alkoxy-substituted $C_1$-$C_4$ alkoxy, —$NR_3R_4$ or fluorinated acetyl or propionyl;

$Y_2$ represents halogen, $C_1$-$C_4$ alkyl, $C_1$-$C_4$ haloalkyl or —CN, or, when $W_2$ represents F, $X_2$ and $Y_2$ taken together represent —O(CH$_2$)$_n$O— wherein n=1 or 2; and $R_3$ and $R_4$ independently represent H or $C_1$-$C_6$ alkyl; and c)

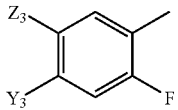

wherein $Y_3$ represents halogen, —CN or —$CF_3$;

$Z_3$ represents F, Cl, —CN, —$NO_2$, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkyl, $C_1$-$C_4$ haloalkoxy, $C_1$-$C_4$ alkoxy-substituted $C_1$-$C_4$ alkyl, $C_1$-$C_4$ alkoxy-substituted $C_1$-$C_4$ alkoxy, —$NR_3R_4$ or fluorinated acetyl or propionyl; and $R_3$ and $R_4$ independently represent H, or $C_1$-$C_6$ alkyl; and Metal represents Mg-halide, Zn-halide, tri-($C_1$-$C_4$ alkyl)tin, lithium, copper, or B(OR$_8$)(OR$_9$), where $R_8$ and $R_9$ are independent of one another, hydrogen, $C_1$-$C_4$ alkyl, or when taken together form an ethylene or propylene group.

2. A compound according to claim 1 selected from the group consisting of:

2-(4-Chloro-2-fluoro-3-methoxyphenyl)-[1,3,2]-dioxaborinane;
2-(4-Chloro-2-fluoro-5-methoxyphenyl)-[1,3,2]-dioxaborinane;
2-(4-Chloro-2-fluoro-3-ethoxyphenyl)-[1,3,2]-dioxaborinane;
2-(4-Chloro-2-fluoro-3-(methylthio)phenyl)-[1,3,2]-dioxaborinane;
2-(4-Chloro-2-fluoro-3-methoxymethylphenyl)-[1,3,2]-dioxaborinane;
2-(4-Chloro-2-fluoro-3-isopropoxyphenyl)-[1,3,2]-dioxaborinane;
2-(4-Chloro-2-fluoro-3-difluoromethylphenyl)-[1,3,2]-dioxaborinane;
2-(4-Chloro-2-fluoro-3-fluoromethylphenyl)-[1,3,2]-dioxaborinane;
4-[1,3,2]-Dioxaborinan-2-yl-3-fluoro-2-methoxybenzonitrile;
2-(4-Chloro-2-fluoro-3-methoxyethoxyphenyl)-[1,3,2]-dioxaborinane;
2-(2,4-Dichloro-3-ethoxyphenyl)-[1,3,2]-dioxaborinane;
2-[4-Chloro-2-fluoro-3-(2,2-difluoroethoxyphenyl]-[1,3,2]-dioxaborinane;
2-(4-Chloro-2-fluoro-5-ethoxyphenyl)-[1,3,2]-dioxaborinane;
2-(2,4-Dichloro-3-(methylthio)phenyl)-[1,3,2]dioxaborinane;
2-Fluoro-3,4-methylenedioxyphenylboronic acid;
2-Fluoro-3-methoxy-4-methylphenylboronic acid;
4-Bromo-2-fluoro-3-methoxyphenylboronic acid;
2-(2-Fluoro-3,4-methylenedioxyphenyl)-[1,3,2]-dioxaborinane;
4-Chloro-3-(diethylamino)-2-fluorophenylboronic acid;
2,4-Dichloro-3-dimethylaminophenylboronic acid;
2-Chloro-4-fluoro-3-methoxyphenylboronic acid;
[3-Chloro-2-fluoro-3-(4,4,5,5-tetramethyl-{1,3,2}dixoborolan-2-yl)-phenyl methyl;
(2-Fluoro-3-methoxy-4-trifluoromethylphenyl)trimethyl stannane;
(3-Butoxy-4-chloro-2-fluorophenyl)trimethyl stannane; and
4-Chloro-2-fluoro-3-(1-fluoro-1-methylethyl)trimethyl stannane.

* * * * *